US008771843B2

(12) United States Patent
Seo et al.

(10) Patent No.: US 8,771,843 B2
(45) Date of Patent: Jul. 8, 2014

(54) FLUORENE DERIVATIVE, ORGANIC COMPOUND, AND LIGHT-EMITTING ELEMENT, LIGHT-EMITTING DEVICE, AND ELECTRONIC DEVICE USING THE COMPOUND

(75) Inventors: Satoshi Seo, Kanagawa (JP); Sachiko Kawakami, Kanagawa (JP); Harue Osaka, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 384 days.

(21) Appl. No.: 13/218,597

(22) Filed: Aug. 26, 2011

(65) Prior Publication Data

US 2012/0049768 A1 Mar. 1, 2012

(30) Foreign Application Priority Data

Aug. 27, 2010 (JP) .................. 2010-190712

(51) Int. Cl.
*H01L 51/54* (2006.01)
(52) U.S. Cl.
USPC ........... 428/690; 428/917; 313/504; 313/506; 257/40; 548/310.7
(58) Field of Classification Search
None
See application file for complete search history.

(56) References Cited

U.S. PATENT DOCUMENTS

| 5,312,707 A | 5/1994 | Ota et al. |
| 5,420,288 A | 5/1995 | Ohta et al. |
| 5,869,929 A | 2/1999 | Eida et al. |
| 6,344,283 B1 | 2/2002 | Inoue et al. |
| 6,623,872 B2 | 9/2003 | Inoue et al. |
| 6,905,788 B2 | 6/2005 | Tyan et al. |
| 7,097,918 B2 | 8/2006 | Inoue et al. |
| 7,651,786 B2 | 1/2010 | Matsuura et al. |
| 7,700,201 B2 | 4/2010 | Seo et al. |
| 7,732,063 B2 | 6/2010 | Matsuura et al. |
| 2002/0102434 A1 | 8/2002 | Inoue et al. |
| 2003/0118866 A1 | 6/2003 | Oh et al. |
| 2004/0110030 A1 | 6/2004 | Inoue et al. |

(Continued)

FOREIGN PATENT DOCUMENTS

| CN | 101030624 A | 9/2007 |
| EP | 0 891 121 A1 | 1/1999 |

(Continued)

OTHER PUBLICATIONS

Goldsmith, C.R. et al., "C—H Bond Activation by a Ferric Methoxide Complex: Modeling the Rate-Determining Step in the Mechanism of Lipoxygenase," J. Am. Chem. Soc., vol. 124, No. 1, 2002, pp. 83-96.

(Continued)

*Primary Examiner* — Dawn Garrett
(74) *Attorney, Agent, or Firm* — Husch Blackwell LLP

(57) ABSTRACT

To provide a novel organic compound having a bipolar property. To reduce power consumption of a light-emitting element, a light-emitting device, and an electronic device. The organic compound has a fluorene skeleton and a structure in which an electron-accepting unit and a hole-accepting unit are bonded through carbon at the 9-position of the fluorene skeleton. The organic compound has a bipolar property and a large band gap. The use of the organic compound makes it possible to reduce power consumption of a light-emitting element, a light-emitting device, and an electronic device.

29 Claims, 17 Drawing Sheets

(56) References Cited

U.S. PATENT DOCUMENTS

| | | |
|---|---|---|
| 2004/0110958 A1 | 6/2004 | Nishiyama et al. |
| 2004/0137274 A1 | 7/2004 | Igarashi |
| 2005/0221124 A1 | 10/2005 | Hwang et al. |
| 2006/0033421 A1 | 2/2006 | Matsuura et al. |
| 2006/0180812 A1 | 8/2006 | Sakata et al. |
| 2007/0009758 A1 | 1/2007 | Funahashi |
| 2007/0196692 A1 | 8/2007 | Ise et al. |
| 2007/0215867 A1 | 9/2007 | Kawakami et al. |
| 2007/0215889 A1 | 9/2007 | Kawakami et al. |
| 2008/0036365 A1 | 2/2008 | Miki et al. |
| 2008/0122345 A1 | 5/2008 | Sakata et al. |
| 2008/0124572 A1 | 5/2008 | Mizuki et al. |
| 2008/0206598 A1 | 8/2008 | Ohsawa et al. |
| 2009/0200918 A1* | 8/2009 | Seo et al. .................. 313/503 |
| 2009/0295278 A1 | 12/2009 | Lee et al. |
| 2010/0060155 A1 | 3/2010 | Seo et al. |
| 2010/0155714 A1 | 6/2010 | Seo et al. |
| 2010/0187978 A1* | 7/2010 | Yu et al. .................. 313/504 |
| 2010/0230666 A1 | 9/2010 | Ohuchi et al. |
| 2010/0270913 A1 | 10/2010 | Matsuura et al. |
| 2010/0277061 A1 | 11/2010 | Matsuura et al. |
| 2010/0301744 A1 | 12/2010 | Osaka et al. |
| 2010/0314612 A1 | 12/2010 | Lee et al. |
| 2011/0095678 A1 | 4/2011 | Ogita et al. |
| 2011/0303901 A1* | 12/2011 | Cheng et al. .................. 257/40 |
| 2012/0056171 A1* | 3/2012 | Kim et al. .................. 257/40 |
| 2013/0112961 A1 | 5/2013 | Seo et al. |

FOREIGN PATENT DOCUMENTS

| | | |
|---|---|---|
| JP | H06-107605 A | 4/1994 |
| JP | 6-220437 | 8/1994 |
| JP | 2002-179630 A | 6/2002 |
| JP | 2003-007467 A | 1/2003 |
| JP | 2005-85599 | 3/2005 |
| JP | 2005-120030 | 5/2005 |
| JP | 2005-320277 | 11/2005 |
| JP | 2007-15933 | 1/2007 |
| JP | 2007-227658 | 9/2007 |
| JP | 2009-010181 A | 1/2009 |
| WO | WO 2005/092857 A1 | 10/2005 |
| WO | WO 2008/147110 | * 12/2008 |
| WO | WO 2010/131930 | * 11/2010 |

OTHER PUBLICATIONS

Onishi, T. et al., "A Method of Measuring an Energy Level," *High Molecular EL Materials Development of Light-Emitting High Molecular Compounds*, Kyoritsu Shuppan, Dec. 25, 2004, p. 64-67 (with English translation, pp. 1-3).

Shih, P.-I. et al, "A Novel Fluorene-Triphenylamine Hybrid That is a Highly Efficient Host Material for Blue-, Green-, and Red-Light-Emitting Electrophosphorescent Devices," *Advanced Functional Materials*, vol. 17, 2007, pp. 3514-3520.

Agata, Y. et al., "Syntheses and Properties of Novel Quarterphenylene-based Materials for Blue Organic Light-emitting Devices," *Chemistry Letters*, 2007, vol. 36, No. 2, pp. 316-317.

Adachi, C. et al., "Durability Characteristics of Aminopyrene Dimer Molecules as an Emitter in Organic Multilayer Electroluminescent Diodes," *Japanese Journal of Applied Physics*, 1996, vol. 35, No. 9A, pp. 4819-4825.

Ge, Z. et al., "Spin-Coated Highly Efficient Phosphorescent Organic Light-Emitting Diodes Based on Bipolar Triphenylamine-Benzimidazole Derivatives," *Advanced Functional Materials*, 2008, vol. 18, Issue 4, pp. 584-590.

Ide, N. et al., "Organic Light Emitting Diode (OLED) and its Application to Lighting Devices," *Proc. SPIE*, 2006, vol. 6333, pp. 63330M-1-63330M-10.

Tanaka, D. et al., "High Luminous Efficiency Blue Organic Light-Emitting Devices Using High Triplet Excited Energy Materials," *Japanese Journal of Applied Physics*, 2007, vol. 46, No. 5, pp. L117-L119.

* cited by examiner

↑ Fluorene skeleton

↑ Fluorene skeleton

FLUORENE DERIVATIVE, ORGANIC COMPOUND, AND LIGHT-EMITTING ELEMENT, LIGHT-EMITTING DEVICE, AND ELECTRONIC DEVICE USING THE COMPOUND

BACKGROUND OF THE INVENTION

1. Field of the Invention

The present invention relates to a fluorene derivative, an organic compound (an organic semiconductor material), and a light-emitting element, a light-emitting device, and an electronic device using the organic compound.

2. Description of the Related Art

An organic compound can take a variety of structures in comparison with an inorganic compound and can be used to synthesize a material having a variety of functions with appropriate molecular design. Owing to these advantages, electronics utilizing a functional organic material has been attracting attention in recent years.

As examples of electronic devices using an organic compound as a functional material, there are solar cells, light-emitting elements, organic transistors, and the like. These are devices in which electric properties and optical properties of organic compounds are utilized. In particular, tremendous progress has been made in light-emitting elements.

It is said that the light emission mechanism of a light-emitting element is as follows: by application of voltage between a pair of electrodes with a light-emitting layer interposed therebetween, electrons injected from a cathode and holes injected from an anode recombine in the luminescence center of the light-emitting layer to form molecular excitons, and when the molecular excitons relax to a ground state, energy is released to emit light. A singlet excitation state (S*) and a triplet excitation state (T*) are known as excited states. Light emission is considered possible through either singlet excitation or triplet excitation. In addition, the statistical generation ratio of the excitation state in the light-emitting element is considered to be as follows: S*:T*=1:3.

As for a compound which converts a singlet excited state to light emission (hereinafter, such a compound is referred to as a "fluorescent compound"), light emission from the triplet excited state (phosphorescence) is not observed but only light emission from the singlet excited state (fluorescence) is observed at room temperature. Therefore, the internal quantum efficiency (the ratio of generated photons to injected carriers) in a light-emitting element using a fluorescent compound is assumed to have a theoretical limit of 25% on the basis of the statistical generation ratio, S*:T*=1:3.

In contrast, when a compound in which a triplet excited state is converted into light emission (hereinafter, such a compound is referred to as a "phosphorescent compound") is used, the internal quantum efficiency can be theoretically 75% to 100%. In other words, emission efficiency that is 3 times to 4 times as much as that of the fluorescence compound can be achieved. For these reasons, in order to achieve a highly efficient light-emitting element, a light-emitting element using a phosphorescent compound has been actively developed recently.

When a light-emitting layer of a light-emitting element is formed using the above phosphorescent compound, in order to suppress concentration quenching of the phosphorescent compound or quenching due to triplet-triplet annihilation (T-T annihilation), the light-emitting layer is often formed so that the phosphorescent compound is dispersed in a matrix of another substance. In that case, a substance serving as a matrix is referred to as a host material, a substance that is dispersed in a matrix, such as a phosphorescent compound, is referred to as a guest material.

In the case where a phosphorescent compound is used as a guest material, a host material is required to have a large energy gap (a difference between the highest occupied molecular orbital level (HOMO level) and the lowest unoccupied molecular orbital level (HOMO level)) or triplet excitation energy (a difference in energy between a ground state and a triplet excited state) higher than that of the phosphorescent compound. Therefore, a substance having such characteristics has been developed.

For example, in Patent Document 1, a substance having a fluorene skeleton, the structural formula of which is shown below, is disclosed as a material suitable for a host material of a light-emitting element.

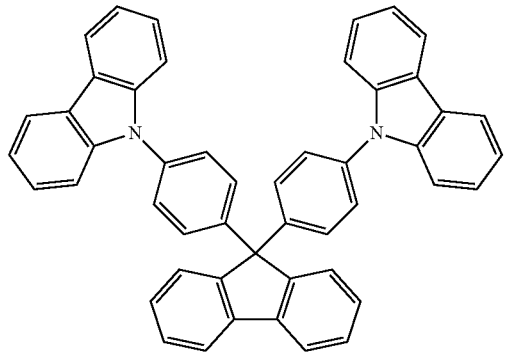 [SMILES: c1ccc2c(c1)-c1ccccc1C2(c1ccc(-n2c3ccccc3c3ccccc32)cc1)c1ccc(-n2c3ccccc3c3ccccc32)cc1]

[Patent Document 1] PCT International Publication No. W2005/092857

SUMMARY OF THE INVENTION

The substance described in Patent Document 1 exhibits a hole-transport property as apparent from its Examples. Therefore, it is expected that holes penetrate a light-emitting layer in the case where the material described in Patent Document 1 is used as a host material of the light-emitting layer. In Patent Document 1, a hole-blocking/electron-transport layer is formed using BAlq, which is a hole-blocking material, in the light-emitting layer on the cathode side in order to prevent holes from penetrating the light-emitting layer. When the substance having the above structure, which is described in Patent Document 1, is used as a host material of a light-emitting layer as described above, a light-emitting region might exist locally at an interface between the light-emitting layer and the electron-transport layer (the hole-blocking layer) because the host material has a hole-transport property. When the light-emitting region locally exists, quenching due to triplet-triplet annihilation (T-T annihilation) is caused, which results in reduction in emission efficiency.

In order to suppress the above, the host material needs to have a bipolar property which enables the host material to be both oxidized and reduced and to be stable to both oxidation and reduction. However, when a skeleton having an electron-transport property and a skeleton having a hole-transport property are directly bonded, decrease in band gap is caused, which makes it difficult to obtain a material having high triplet excitation energy. In addition, when a substituent is introduced between the skeleton having an electron-transport property and the skeleton having a hole-transport property to expand a conjugation system, decrease in band gap and decrease in triplet excitation energy are caused.

In view of the above, an object of one embodiment of the present invention is to provide a novel organic semiconductor material having a bipolar property and a large band gap or high triplet excitation energy.

An object of one embodiment of the present invention is to reduce driving voltage of a light-emitting element. In addition, an object of one embodiment of the present invention is to improve emission efficiency of a light-emitting element.

In addition, an object of one embodiment of the present invention is to reduce power consumption of a light-emitting element, a light-emitting device, and an electronic device.

The inventors have found out that a material which has both an electron-transport property and a hole-transport property (i.e., a bipolar property) while maintaining a large energy gap can be obtained by bonding a skeleton having an electron-transport property and a skeleton having a hole-transport property through carbon at the 9-position of fluorene.

Specifically, the inventors have found out that a material represented by General Formula (G1) has both a large energy gap and a bipolar property.

Therefore, one embodiment of the present invention is an organic compound (an organic semiconductor material) represented by General Formula (G1).

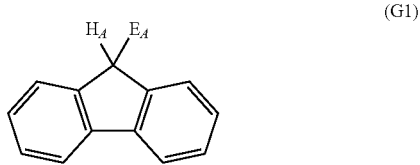

In the formula, $E_A$ represents an electron-accepting unit and $H_A$ represents a hole-accepting unit. Note that the electron-accepting unit has higher electron affinity and ionization potential than the hole-accepting unit. In addition, the electron-accepting unit is a skeleton having an electron-transport property, and the hole-accepting unit is a skeleton having a hole-transport property.

Among three substances that are a compound $E_AH$ derived by replacing a fluorene group bonded to the electron-accepting unit $E_A$ with hydrogen, a compound $H_AH$ derived by replacing a fluorene group bonded to the hole-accepting unit $H_A$ with hydrogen, and fluorene, the compound $E_AH$ has the highest electron affinity, and the compound $H_AH$ has the smallest ionization potential. Note that in the above structure, the 1- to 8-positions of fluorene may have substituents. As each of the substituents, either an alkyl group having 1 to 6 carbon atoms or an aryl group having 6 to 13 carbon atoms can be selected.

In the above structure, the compound $E_AH$ derived by replacing the fluorene group bonded to the electron-accepting unit $E_A$ with hydrogen preferably has an electron affinity of greater than or equal to 2.0 eV and less than or equal to 4.0 eV, and the compound $H_AH$ derived by replacing the fluorene group bonded to the hole-accepting unit $H_A$ with hydrogen preferably has an ionization potential of greater than or equal to 4.5 eV and less than or equal to 6.5 eV. In particular, in the case where the organic semiconductor material is used for a light-emitting element, the compound $E_AH$ derived by replacing the fluorene group bonded to the electron-accepting unit $E_A$ with hydrogen preferably has an electron affinity of greater than or equal to 2.0 eV and less than or equal to 3.0 eV, and the compound $H_AH$ derived by replacing the fluorene group bonded to the hole-accepting unit $H_A$ with hydrogen preferably has an ionization potential of greater than or equal to 5.0 eV and less than or equal to 6.0 eV.

In the above structure, as examples of the substituent represented by $E_A$, a nitrogen-containing 6-membered aromatic ring, a 1,2-azole group, a 1,3-azole group, a polyazole group, a phenyl group having any of these groups, and the like are given.

In the above structure, as examples of the substituent represented by $H_A$, a phenyl group having a π-electron rich heteroaromatic substituent, a phenyl group having a diarylamino group, and the like are given.

A fluorene derivative represented by General Formula (G1) has a bipolar property, and thus can be favorably used, as an organic semiconductor material, for a light-emitting element or an organic device such as an organic transistor.

Therefore, another embodiment of the present invention is a light-emitting element including the organic semiconductor material represented by General Formula (G1), that is, a light-emitting element including the organic semiconductor material represented by General Formula (G1) between a pair of electrodes.

In particular, since the organic semiconductor material represented by General Formula (G1) has high triplet excitation energy, it has more prominent effect when being used for a light-emitting element together with a phosphorescent compound.

Therefore, one embodiment of the present invention is a light-emitting element in which the organic semiconductor material represented by General Formula (G1) is contained between a pair of electrodes and a phosphorescent compound is contained in a light-emitting layer.

In addition, the organic semiconductor material represented by General Formula (G1) has a bipolar property, and thus is preferably used for a light-emitting layer.

Further, the present invention includes, in its category, a light-emitting device including a light-emitting element containing the organic semiconductor material represented by General Formula (G1).

Therefore, one embodiment of the present invention is a light-emitting device including a light-emitting element containing the organic semiconductor material represented by General Formula (G1) and a control circuit which controls light emission from the light-emitting element.

Note that the light-emitting device in this specification includes, in its category, an image display device, a light-emitting device, and a light source (including a lighting device). Further, the following are all included in the category of the light-emitting device: a module in which a connector, for example, a flexible printed circuit (FPC), a tape automated bonding (TAB) tape, or a tape carrier package (TCP) is attached to a panel provided with a light-emitting element; a module provided with a printed wiring board at the end of the TAB tape or the TCP; and a module in which an IC (integrated circuit) is directly mounted to a light-emitting element by a chip on glass (COG) method Further, an electronic device using the light-emitting element of one embodiment of the present invention in a display portion is also included in the scope of the present invention. Therefore, an embodiment of the present invention is an electronic device having a display portion which includes the above light-emitting element and a control circuit which controls light emission from the light-emitting element.

The organic semiconductor material of one embodiment of the present invention is a novel material that has a bipolar property and a large energy gap or high triplet excitation energy.

Further, application of one embodiment of the present invention makes it possible to reduce driving voltage of a light-emitting element and improve emission efficiency of a light-emitting element.

Further, application of one embodiment of the present invention makes it possible to reduce power consumption of a light-emitting element, a light-emitting device, and an electronic device.

DETAILED DESCRIPTION OF THE INVENTION

Figure 1:
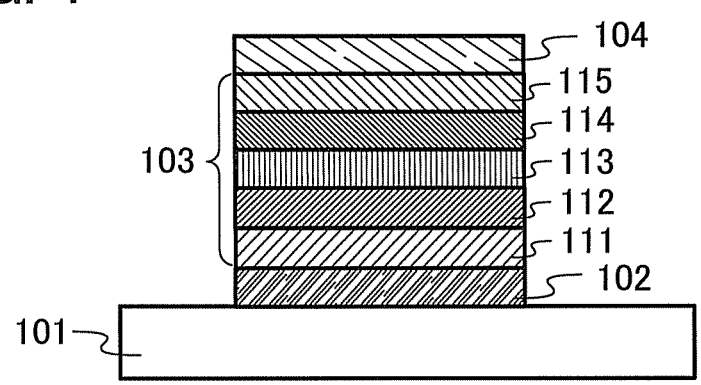
FIG. 1 illustrates a light-emitting element of the present invention.

Hereinafter, Embodiments and Examples of the present invention will be described with reference to the drawings. Note that the present invention is not limited to the description given below, and it will be easily understood by those skilled in the art that various changes and modifications can be made without departing from the spirit and scope of the present invention. Therefore, the present invention should not be construed as being limited to the description in Embodiments and Examples below.

Embodiment 1

In this embodiment, an organic semiconductor material below will be described as an example of an organic compound of the present invention.

The organic semiconductor material according to one embodiment of the present invention has a fluorene skeleton and a structure in which an electron-accepting unit and a hole-accepting unit are bonded through carbon at the 9-position of the fluorene skeleton.

Specifically, the organic semiconductor material of this embodiment is an organic semiconductor material represented by General Formula (G1).

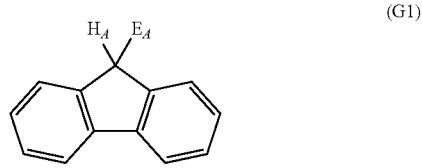

In the formula, $E_A$ represents an electron-accepting unit and $H_A$ represents a hole-accepting unit. Note that in the case where a substance derived by replacing a fluorene group bonded to $H_A$ with hydrogen is represented by $H_A H$ and a substance derived by replacing a fluorene group bonded to $E_A$ with hydrogen is represented by $E_A H$, among $H_A H$, $E_A H$, and fluorene, $E_A H$ has the highest electron affinity and $H_A H$ has the smallest ionization potential. In addition, in the formula, the 1- to 8-positions of fluorene may have substituents. As the substituents, either an alkyl group having 1 to 6 carbon atoms or an aryl group having 6 to 13 carbon atoms can be selected.

An organic semiconductor material having such a structure has an electron-accepting unit and a hole-accepting unit in its molecule, and thus is a bipolar material which can transport both electrons and holes.

In some cases, a compound, even if it has an electron-accepting unit and a hole-accepting unit in a molecule, does not have a bipolar property due to interaction of the units. In contrast, in the organic semiconductor material represented by General Formula (G1), the electron-accepting unit $E_A$ and the hole-accepting unit $H_A$ are bonded through carbon at the 9-position of fluorene; thus, intramolecular interaction is suppressed, which allows the organic semiconductor material to have a bipolar property. In a similar manner, when extension of conjugation is suppressed by carbon at the 9-position of fluorene, an organic semiconductor material having a large energy gap or high triplet excitation energy is obtained.

Note that it is preferable that the electron affinity of the organic semiconductor material represented by General Formula (G1) be greater than or equal to 2.0 eV and less than or equal to 4.0 eV. In particular, in the case where the organic semiconductor material is used for a light-emitting element, in consideration of the electron affinity of a general organic material used for a light-emitting element, the electron affinity of the organic semiconductor material is more preferably greater than or equal to 2.0 eV and less than or equal to 3.0 eV. Here, as described above, intramolecular interaction of the electron-accepting unit $E_A$ and the hole-accepting unit $H_A$ is suppressed in the organic semiconductor material represented by General Formula (G1); thus, the electron affinity of the organic semiconductor material represented by General Formula (G1) is substantially the same as that of the substance $E_A H$ derived by replacing a fluorene group bonded to $E_A$ is substituted with hydrogen, which has the highest electron affinity. For that reason, in the case where the electron-accepting unit $E_A$ is selected, it is preferable to select a unit such that the compound represented by $E_A H$ have an electron affinity of greater than or equal to 2.0 eV and less than or equal to 4.0 eV. Moreover, in the case where the organic semiconductor material represented by General Formula (G1) is used for a light-emitting element, it is preferable to select a unit such that the compound represented by $E_A H$ have an electron affinity of greater than or equal to 2.0 eV and less than or equal to 3.0 eV, as the electron-accepting unit $E_A$.

Note that it is preferable that the ionization potential of the organic semiconductor material represented by General Formula (G1) be greater than or equal to 4.5 eV and less than or equal to 6.5 eV. In particular, in the case where the organic semiconductor material represented by General Formula (G1) is used for a light-emitting element, in consideration of the ionization potential of a general organic material used for a light-emitting element, the ionization potential of the organic semiconductor material is more preferably greater than or equal to 5.0 eV and less than or equal to 6.0 eV. Here, intramolecular interaction of the electron-accepting unit and the hole-accepting unit is suppressed in the organic semiconductor material represented by General Formula (G1); thus, the ionization potential of the organic semiconductor material represented by General Formula (G1) is substantially the same as that of the substance $H_AH$ derived by replacing a fluorene group bonded to $H_A$ with hydrogen, which has the smallest ionization potential. For that reason, in the case where the hole-accepting unit $H_A$ is selected, it is preferable to select a unit such that the compound represented by $H_AH$ have an ionization potential of greater than or equal to 4.5 eV and less than or equal to 6.5 eV. Moreover, in the case where the organic semiconductor material represented by General Formula (G1) is used for a light-emitting element, it is preferable to select a unit such that the compound represented by $H_AH$ have an ionization potential of greater than or equal to 5.0 eV and less than or equal to 6.0 eV, as the hole-accepting unit $H_A$.

As described above, in the organic semiconductor material of this embodiment, the electron-accepting unit and the hole-accepting unit are bonded through carbon at the 9-position of fluorene, so that extension of conjugation is suppressed; thus, the organic semiconductor material can have a large band gap or high triplet excitation energy as well as both high electron affinity of the electron-accepting unit $E_A$ and small ionization potential of the hole-accepting unit $H_A$. In addition, interaction of the electron-accepting unit and the hole-accepting unit is suppressed, which makes it possible to obtain an organic semiconductor material having a bipolar property.

As the electron-accepting unit $E_A$, a π-electron deficient heteroaromatic substituent is preferable so that the electron-accepting unit $E_A$ has high electron affinity. As the π-electron deficient heteroaromatic substituent, the following are given: a nitrogen-containing 6-membered aromatic ring (note that the nitrogen-containing 6-membered aromatic ring includes a condensed aromatic hydrocarbon and a nitrogen-containing 6-membered condensed aromatic ring), a 1,2-azole group (note that the 1,2-azole includes a condensed aromatic hydrocarbon and a nitrogen-containing 6-membered condensed aromatic ring), a 1,3-azole group (note that the 1,3-azole includes a condensed aromatic hydrocarbon and a nitrogen-containing 6-membered condensed aromatic ring), a polyazole group (note that the polyazole includes a condensed aromatic hydrocarbon and a nitrogen-containing 6-membered condensed aromatic ring), and the like. In addition, a phenyl group having any of these groups is also effective as the electron-accepting unit $E_A$. In particular, a nitrogen-containing 6-membered aromatic ring, a 1,3-azole group, a polyazole group, and a phenyl group having any of these groups have relatively high electron affinity, are stable to reduction, and exhibits a high electron-transport property, and thus are preferably selected as the electron-accepting unit $E_A$.

As examples of the nitrogen-containing 6-membered aromatic ring, the following are given: a substituted or unsubstituted pyridyl group, a substituted or unsubstituted pyrazinyl group, a substituted or unsubstituted pyrimidinyl group, a substituted or unsubstituted pyridazinyl group, a substituted or unsubstituted 1,2,4-triazinyl group, a substituted or unsubstituted 1,3,5-triazinyl group, a substituted or unsubstituted quinolyl group, a substituted or unsubstituted isoquinolyl group, a substituted or unsubstituted 1,5-naphthyridinyl group, a substituted or unsubstituted 1,6-naphthyridinyl group, a substituted or unsubstituted 1,7-naphthyridinyl group, a substituted or unsubstituted 1,8-naphthyridinyl group, a substituted or unsubstituted 2,6-naphthyridinyl group, a substituted or unsubstituted 2,7-naphthyridinyl group, a substituted or unsubstituted quinoxalinyl group, a substituted or unsubstituted dibenzoquinoxaline, a substituted or unsubstituted quinazolinyl group, a substituted or unsubstituted phthalazinyl group, a substituted or unsubstituted cinnolinyl group, a substituted or unsubstituted phenanthridinyl group, a substituted or unsubstituted 1,10-phenanthrolinyl group, and the like.

As examples of the 1,2-azole group, the following are given: a substituted or unsubstituted pyrazolyl group, a substituted or unsubstituted isoxazolyl group, a substituted or unsubstituted isothiazolyl group, a substituted or unsubstituted indazolyl group, a substituted or unsubstituted 1,2-benzoisoxazolyl group, a substituted or unsubstituted 1,2-benzoisothiazolyl group, a substituted or unsubstituted 2,1-benzoisoxazolyl group, a substituted or unsubstituted 2,1-benzoisothiazolyl group, and the like.

As examples of the 1,3-azole group, the following are given: a substituted or unsubstituted imidazolyl group, a substituted or unsubstituted oxazolyl group, a substituted or unsubstituted thiazolyl group, a substituted or unsubstituted 1H-benzimidazolyl group, a substituted or unsubstituted benzoxazolyl group, a substituted or unsubstituted benzothiazolyl group, an imidazo[1,2-a]pyridyl group, and the like.

As examples of the polyazole group, the following are given: a substituted or unsubstituted 1H-1,2,3-triazolyl group, a substituted or unsubstituted 1,2,5-oxadiazolyl group, a substituted or unsubstituted 1,2,5-thiadiazolyl group, a substituted or unsubstituted 1H-1,2,4-triazolyl group, a substituted or unsubstituted 4H-1,2,4-triazolyl group, a substituted or unsubstituted 1,2,4-oxadiazolyl group, a substituted or unsubstituted 1,2,4-thiadiazolyl group, a substituted or unsubstituted 1,3,4-oxadiazolyl group, a substituted or unsubstituted 1,3,4-thiadiazolyl group, a substituted or unsubstituted 1H-benzotriazolyl group, a substituted or unsubstituted 2H-benzotriazolyl group, a substituted or unsubstituted 2,1,3-benzoxadiazolyl group, a substituted or unsubstituted 2,1,3-benzothiadiazolyl group, and the like.

Note that in the case where the above nitrogen-containing 6-membered aromatic ring, 1,2-azole group, 1,3-azole group, and polyazole group each have another substituent, the following are given as the substituent: an aryl group such as a phenyl group, a tolyl group, or a naphthyl group; a heteroaromatic group such as a pyridyl group, a quinolyl group, or an isoquinolyl group; an alkyl group such as a methyl group, an ethyl group, an isopropyl group, a tert-butyl group; and the like.

As specific examples of the electron-accepting unit $E_A$ in the case where the phenyl group having the nitrogen-containing 6-membered aromatic ring (note that the nitrogen-containing 6-membered aromatic ring includes a condensed aromatic hydrocarbon and a nitrogen-containing 6-membered condensed aromatic ring) is applied as the electron-accepting unit $E_A$, the following are given: a (2-pyridyl)phenyl group, a (5-methyl-2-pyridyl)phenyl group, a (6-methyl-2-pyridyl)phenyl group, a (3-phenyl-2-pyridyl)phenyl group, a (6-phenyl-2-pyridyl)phenyl group, a (3-pyridyl)phenyl group, a (6-methyl-3-pyridyl)phenyl group, a (2,2':6',2''-terpyridin-4'- yl)phenyl group, a (3-phenylpyrazin-2-yl)phenyl group, a (3,5,6-triphenylpyrazin-2-yl)phenyl group, a (pyrimidin-4-yl)phenyl group, a (6-methylpyrimidin-4-yl)phenyl group, a (6-phenylpyrimidin-4-yl)phenyl group, a (pyrimidin-5-yl)phenyl group, (2,4,6-triphenylpyrimidin-5-yl)phenyl group, a (6-phenylpyridazin-3-yl)phenyl group, a (3-methyl-1,2,4-triazin-6-yl)phenyl group, a (4,6-diphenyl-1,3,5-triazin-2-yl)phenyl group, a (3-quinolyl)phenyl group, a (8-quinolyl)phenyl group, a (2,4-dimethyl-8-quinolyl)phenyl group, a (4-isoquinolyl)phenyl group, a (1,5-naphthyridin-3-yl)phenyl group, a (1,6-naphthyridin-4-yl)phenyl group, a (5,7-dimethyl-1,6-naphthyridin-4-yl)phenyl group, a (5-methyl-1,6-naphthyridin-2-yl)phenyl group, a (1,7-naphthyridin-8-yl)phenyl group, a (1,8-naphthyridin-2-yl)phenyl group, a (3-methyl-1,8-naphthyridin-2-yl)phenyl group, a (1,8-naphthyridin-3-yl)phenyl group, a (2-methyl-1,8-naphthyridin-3-yl)phenyl group, (1,8-naphthyridin-4-yl)phenyl group, a (2,6-naphthyridin-1-yl)phenyl group, (2,7-naphthyridin-3-yl)phenyl group, a (quinoxalin-2-yl)phenyl group, (3-methylquinoxalin-2-yl)phenyl group, a (3-isopropylquinoxalin-2-yl)phenyl group, a (3-phenylquinoxalin-2-yl)phenyl group, a (quinazolin-4-yl)phenyl group, a (phthalazin-1-yl)phenyl group, (3-phenylcinnolin-4-yl)phenyl group, (phenanthridin-6-yl)phenyl group, (1,10-phenanthrolin-2-yl)phenyl group, (1,10-phenanthrolin-3-yl)phenyl group, and the like.

Further, as specific examples of the electron-accepting unit $E_A$ in the case where the phenyl group having the 1,2-azole group (note that the 1,2-azole includes a condensed aromatic hydrocarbon and a nitrogen-containing 6-membered condensed aromatic ring) is applied as the electron-accepting unit $E_A$, the following are given: a (3,5-diphenyl-1H-pyrazol-1-yl)phenyl group, a (1,5-diphenyl-1H-pyrazol-3-yl)phenyl group, a (5-phenylisoxazol-3-yl)phenyl group, a (5-phenylisothiazol-3-yl)phenyl group, a (3-methyl-1,2-benzoisoxazol-5-yl)phenyl group, a (3-methyl-1,2-benzoisothiazol-5-yl)phenyl group, a (2,1-benzoisoxazol-3-yl)phenyl group, a (2,1-benzoisothiazol-3-yl)phenyl group, and the like.

Further, as specific examples of the electron-accepting unit $E_A$ in the case where the phenyl group having the 1,3-azole group (note that the 1,3-azole includes a condensed aromatic hydrocarbon and a nitrogen-containing 6-membered condensed aromatic ring) is applied as the electron-accepting unit $E_A$, the following are given: a (2,4-diphenyl-1H-imidazol-1-yl)phenyl group, a (2-phenyloxazol-4-yl)phenyl group, a (2-phenylthiazol-4-yl)phenyl group, a (1-methyl-1H-benzimidazol-2-yl)phenyl group, a (1-ethyl-1H-benzimidazol-2-yl)phenyl group, a (1-phenyl-1H-benzimidazol-2-yl)phenyl group, a (2-phenyl-1H-benzimidazol-1-yl)phenyl group, a (benzoxazol-2-yl)phenyl group, a (5-phenylbenzoxazol-2-yl)phenyl group, a 4-[5-(p-tolyl)benzoxazol-2-yl]phenyl group, a (benzothiazol-2-yl)phenyl group, a (5-phenyl benzothiazol-2-yl)phenyl group, a 4-[5-(p-tolyl)benzothiazol-2-yl]phenyl group, a (imidazo[1,2-a]pyridin-2-yl)phenyl group, a (5-phenylimidazo[1,2-a]pyridin-2-yl)phenyl group, and the like.

Further, as specific examples of the electron-accepting unit $E_A$ in the case where the phenyl group having the polyazole group (note that the polyazole includes a condensed aromatic hydrocarbon and a nitrogen-containing 6-membered condensed aromatic ring) is applied as the electron-accepting unit $E_A$, the following are given: a (1-phenyl-1H-1,2,3-triazol-4-yl)phenyl group, a (4-phenyl-1,2,5-oxadiazol-3-yl)phenyl group, a (4-phenyl-1,2,5-thiadiazol-3-yl)phenyl group, a (5-methyl-1-phenyl-1H-1,2,4-triazol-3-yl)phenyl group, a (4,5-diphenyl-4H-1,2,4-triazol-3-yl)phenyl group, a [4-(4-sec-butylphenyl)-5-phenyl-4H-1,2,4-triazol-3-yl]phenyl group, a (3,5-diphenyl-4H-1,2,4-triazol-4-yl)phenyl group, a [4-phenyl-5-(2-pyridyl)-4H-1,2,4-triazol-3-yl]phenyl group, a [5-(2-pyridyl)-4-(4-pyridyl)-4H-1,2,4-triazol-3-yl]phenyl group, a [5-phenyl-4-(8-quinolyl)-4H-1,2,4-triazol-3-yl]phenyl group, a (3-phenyl-1,2,4-oxadiazol-5-yl)phenyl group, a (3-phenyl-1,2,4-thiadiazol-5-yl)phenyl group, a (5-phenyl-1,3,4-oxadiazol-2-yl)phenyl group, a [5-(4-tert-butylphenyl)-1,3,4-oxadiazol-2-yl]phenyl group, a [5-(2-naphthyl)-1,3,4-oxadiazol-2-yl]phenyl group, a {5-[4-(1-naphthyl)phenyl]-1,3,4-oxadiazol-2-yl}-phenyl group, a {5-[4-(2-naphthyl)phenyl]-1,3,4-oxadiazol-2-yl}phenyl group, a (5-phenyl-1,3,4-thiadiazol-2-yl)phenyl group, a [5-(4-tert-butylphenyl)-1,3,4-thiadiazol-2-yl]phenyl group, a [5-(2-naphthyl)-1,3,4-thiadiazol-2-yl]phenyl group, a {5-[4-(1-naphthyl)phenyl]-1,3,4-thiadiazol-2-yl}phenyl group, a {5-[4-(2-naphthyl)phenyl]-1,3,4-thiadiazol-2-yl}phenyl group, and the like.

As the hole-accepting unit $H_A$, a phenyl group having a π-electron rich heteroaromatic substituent or a phenyl group having a diarylamino group, which has a small ionization potential is preferably used. Note that as for the diarylamino group, aryl groups may be directly bonded to form a carbazole ring or they may be bonded through nitrogen, oxygen, or sulfur to form a ring. In particular, the diarylamino group (including the case where aryl groups are directly bonded to form a carbazole ring or they are bonded through nitrogen, oxygen, or sulfur to form a ring) is preferable because it is stable to oxidation and exhibits a high hole-transport property as well as having a relatively small ionization potential.

As the π-electron rich heteroaromatic substituent bonded to the phenyl group, a monohetero 5-membered aromatic ring group (note that the monohetero 5-membered aromatic ring includes a condensed aromatic hydrocarbon and a nitrogen-containing 6-membered condensed aromatic ring) is given. Specifically, the following are given: a substituted or unsubstituted pyrrolyl group, a substituted or unsubstituted furyl group, a substituted or unsubstituted thienyl group, a substituted or unsubstituted indolyl group, a substituted or unsubstituted benzofuryl group, a substituted or unsubstituted dibenzofuranyl group, a substituted or unsubstituted benzothienyl group, a substituted or unsubstituted dibenzothiophenyl group, a substituted or unsubstituted isoindolyl group, a substituted or unsubstituted isobenzofuryl group, a substituted or unsubstituted isobenzothienyl group, a substituted or unsubstituted carbazolyl group, and the like.

As the diarylamino group bonded to the phenyl group, the following are given: a substituted or unsubstituted diphenylamino group, a substituted or unsubstituted N-(1-naphthyl)-N-phenylamino group, a substituted or unsubstituted N-(2-naphthyl)-N-phenylamino group, and the like. Further, as for the diarylamino group, aryl groups may be directly bonded to form a carbazole ring or they may be bonded through nitrogen, oxygen, or sulfur to form a ring. A hole-accepting unit in that case is a substituted or unsubstituted 9H-carbazol-9-yl group, a substituted or unsubstituted 10H-phenoxazin-10-yl group, a substituted or unsubstituted 10H-phenothiazin-10-yl group, a substituted or unsubstituted 5,10-dihydrophenazin-5-yl group.

Note that in the case where the above monohetero 5-membered aromatic ring group and diarylamino group each have a substituent, the following are given as the substituent: an aryl group such as a phenyl group, tolyl group, or a naphthyl group; a heteroaryl group such as a pyridyl group, a quinolyl group, or an isoquinolyl group; an alkyl group such as a methyl group, an ethyl group, an isopropyl group, a tert-butyl group; and the like.

As specific examples of the hole-accepting unit $H_A$ having the monohetero 5-membered aromatic ring group (note that monohetero 5-membered aromatic ring includes a condensed aromatic hydrocarbon and a nitrogen-containing 6-membered condensed aromatic ring), the following are given: (1-methyl-5-phenyl-1H-pyrrol-2-yl)phenyl group, (1,5-diphenyl-1H-pyrrol-2-yl)phenyl group, (2,5-diphenyl-1H-pyrrol-1-yl)phenyl group, (5-phenyl-2-furyl)phenyl group, (5-phenyl-2-thienyl)phenyl group, (1H-indol-1-yl)phenyl group, (2-methyl-1H-indol-1-yl)phenyl group, (2-phenyl-1H-indol-1-yl)phenyl group, (1-phenyl-1H-indol-2-yl)phenyl group, (2-benzofuryl)phenyl group, (2-benzothienyl)phenyl group, (2,3-diphenylisoindol-1-yl)phenyl group, (3-phenylisofuryl)phenyl group, (3-phenylisothienyl)phenyl group, and the like.

As specific examples of the hole-accepting unit $H_A$ having the diarylamino group (including the case where aryl groups are directly bonded to form a carbazole ring or a case where aryl groups are bonded through nitrogen, oxygen, or sulfur), the following are given: (diphenylamino)phenyl group, a [N-(biphenyl-4-yl)-N-phenylamino]phenyl group, a {N-[4-(1-naphthyl)phenyl]-N-phenylamino}phenyl group, a {N-[4-(2-naphthyl)phenyl]-N-phenylamino}phenyl group, {N,N-bis[4-(1-naphthyl)phenyl]amino}phenyl group, a [N-(1-naphthyl)-N-phenylamino]phenyl group, a (9H-carbazol-9-yl)phenyl group, a 4-(3-phenyl-9H-carbazol-9-yl)phenyl group, a [3-(1-naphthyl)-9H-carbazol-9-yl]phenyl group, a [3-(2-naphthyl)-9H-carbazol-9-yl]phenyl group, a (10-phenyl-5,10-dihydrophenazin-5-yl)phenyl group, a (10H-phenoxazin-10-yl)phenyl group, a (10H-phenothiazin-10-yl)phenyl group, and the like.

The organic semiconductor material represented by General Formula (G1) has a bipolar property having an electron-transport property and a hole-transport property. Thus, in the case where the organic semiconductor material is applied to a light-emitting element, driving voltage can be reduced. In the case where the organic semiconductor material is applied especially to a light-emitting layer, a prominent effect can be obtained.

Further, in the case where the organic semiconductor material represented by General Formula (G1) is used as a host material of a light-emitting layer, localization of a light-emitting region can be suppressed, and concentration quenching of a substance having a high light-emitting property or quenching due to triplet-triplet annihilation (T-T annihilation) can be suppressed. Thus, high emission efficiency can be realized.

Further, the organic semiconductor material represented by General Formula (G1) has a fluorene skeleton in the center, and thus has a sterically bulky structure. The sterically bulky structure makes it difficult for the organic semiconductor material to be crystallized in the case of being formed as a film. Thus, the organic semiconductor material easily keeps an amorphous state, and thus is suitable for a light-emitting element. The organic semiconductor material is also suitable for a light-emitting element for the following reasons: excellent morphology and stable film quality.

Further, since the skeleton which bonds the electron-transport unit $E_A$ and the hole-transport unit $H_A$ is fluorene and has not so large molecular weight; and thus, the organic semiconductor material has excellent solubility, is easily purified, and can suppress reduction in element lifetime due to an impurity. In addition, for the same reason, the organic semiconductor material has an appropriate sublimation property and is easily evaporated. Moreover, the fluorene skeleton has less intramolecular reaction such as cyclization even at the time of light irradiation, and thus can exist stably.

Further, the organic semiconductor material represented by General Formula (G1) has high triplet excitation energy. Thus, the organic semiconductor material can be used for a light-emitting element containing a phosphorescent compound as a luminescence center material as well as a light-emitting element containing a fluorescent compound as a luminescence center material. In particular, in the case where the organic semiconductor material is used together with a phosphorescent compound which exhibits light emission with a short wavelength, a prominent effect can be obtained.

Moreover, the organic semiconductor material according to the present invention has a large energy gap (a difference between the highest occupied molecular orbital (HOMO level) and the lowest unoccupied molecular orbital level (LUMO level)). Thus, the organic semiconductor material can be used for a light-emitting element together with a fluorescent compound. In particular, in the case where the organic semiconductor material is used together with a fluorescent compound which exhibits light emission with a short wavelength, a prominent effect can be obtained.

A fluorene derivative represented by General Formula (G2-1) below is a specific example of the organic semiconductor material represented by General Formula (G1).

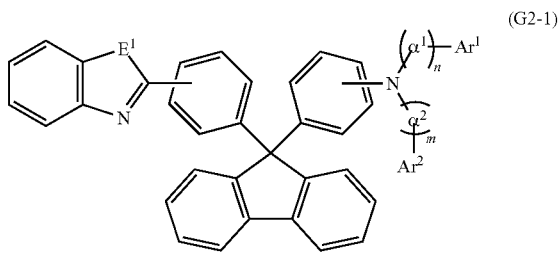

(G2-1)

Note that in General Formula (G2-1), $E^1$ represents a nitrogen atom or an oxygen atom, and a phenyl group or a biphenyl group is bonded to $E^1$ in the case where $E^1$ is a nitrogen atom. In addition, m and n separately represent 0 or 1, and $\alpha^1$ and $\alpha^2$ separately represent an arylene group such as a phenylene group or a biphenyldiyl group. In addition, $Ar^1$ and $Ar^2$ separately represent any of a phenyl group, a naphthyl group, a phenanthryl group, and a triphenylenyl group.

Note that in General Formula (G2-1), it is preferable that $\alpha^1$ and $\alpha^2$ be a phenylene group. In addition, it is preferable that $Ar^1$ and $Ar^2$ be a phenyl group. In other words, a fluorene derivative represented by General Formula (G2-2) below is preferable.

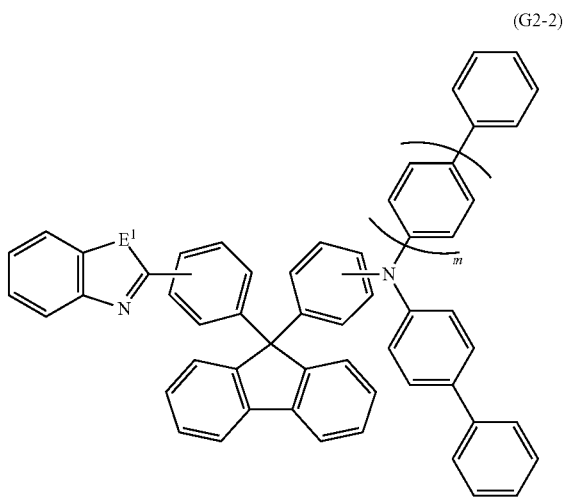

(G2-2)

Note that in General Formula (G2-2), $E^1$ represents a nitrogen atom or an oxygen atom, and a phenyl group or a biphenyl group is bonded to $E^1$ in the case where $E^1$ is a nitrogen atom. In addition, m represents 0 or 1.

In the fluorene derivative represented by General Formula (G2-2), $E^1$ is preferably a nitrogen atom to which a phenyl group is bonded, and such a fluorene derivative is represented by General Formula (G2-3) below.

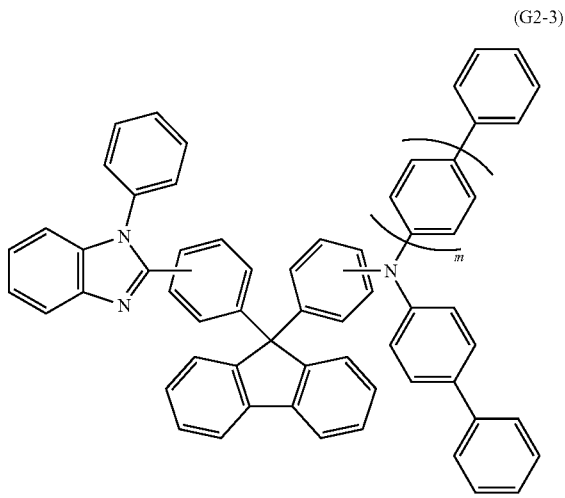

(G2-3)

Note that in the formula, m represents 0 or 1.

In the fluorene derivative represented by General Formula (G2-3), a phenylene group which is between a fluorene group and a benzimidazole group is preferably a para-substituted phenylene group, and m is preferably 0. In other words, a fluorene derivative represented by Structural Formula (1) below is more preferable.

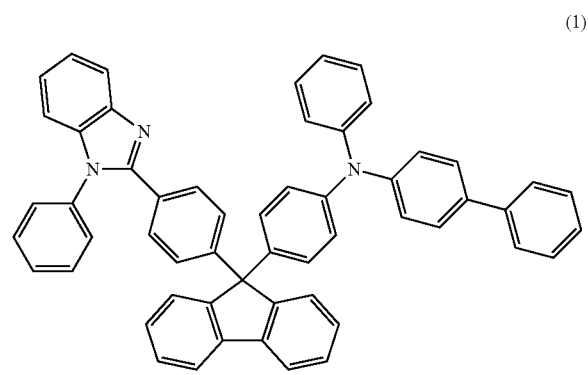

(1)

The above fluorene derivative has a bipolar property having both an electron-transport property and a hole-transport property. Thus, in the case where the fluorene derivative is applied to a light-emitting element, driving voltage can be reduced. In particular, in the case where the organic semiconductor material is applied to a light-emitting layer, a prominent effect can be obtained.

Further, in the case where the above fluorene derivative is used as a host material of a light-emitting layer, localization of a light-emitting region can be suppressed, and concentration quenching of a substance having a high light-emitting property or quenching due to triplet-triplet annihilation (T-T annihilation) can be suppressed. Thus, high emission efficiency can be realized.

Further, the above fluorene derivative has a fluorene skeleton in the center, and thus has a sterically bulky structure. The sterically bulky structure makes it difficult for the organic semiconductor material to be crystallized in the case of being formed as a film. Thus, the organic semiconductor material easily keeps an amorphous state, and thus is suitable for a light-emitting element. The organic semiconductor material is also suitable for the following reasons: excellent morphology and stable film quality.

Further, since the skeleton which bonds the electron-transport unit $E_A$ and the hole-transport unit $H_A$ is fluorene and has not so large molecular weight; and thus, the organic semiconductor material has excellent solubility, is easily purified, and can suppress reduction in element lifetime due to an impurity. In addition, for the same reason, the organic semiconductor material has an appropriate sublimation property and is easily evaporated. Moreover, the fluorene skeleton has less intramolecular reaction such as reduction even at the time of light irradiation, and thus can exist stably.

Further, the above fluorene derivative has high triplet excitation energy. Thus, the fluorene derivative can be used for a light-emitting element containing a phosphorescent compound as a luminescence center as well as a light-emitting element containing a fluorescent compound as a luminescence center material. In particular, in the case where the fluorene derivative is used together with a phosphorescent compound which exhibits light emission with a short wavelength, a prominent effect can be obtained.

Embodiment 2

In this embodiment, a synthesis method of the organic semiconductor material represented by General Formula (G1) below, which is described in Embodiment 1, will be described. The organic semiconductor material described in Embodiment 1 is a material in which both an electron-transport unit and a hole-transport unit are bonded to carbon at the 9-position of fluorene. In other words, the organic semiconductor material is an asymmetric substance. However, two hydrogen bonded to a carbon at the 9-position of unsubstituted fluorene are completely the same in terms of energy and cannot be distinguished from each other, which makes it very difficult to synthesize the organic semiconductor material by coupling reaction of unsubstituted fluorene and the electron-transport unit and the hole-transport unit. The present inventors have conducted diligent studies in view of the above and have found out that the organic semiconductor material described in Embodiment 1 can be obtained by a synthesis method described below.

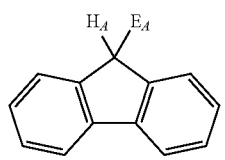

(G1)

In the formula, $E_A$ represents an electron-accepting unit and $H_A$ represents a hole-accepting unit. Note that in the case where a substance derived by replacing a fluorene group bonded to $H_A$ with H is represented by $H_A H$ and a substance derived by replacing a fluorene group bonded to $E_A$ with H is represented by $E_A H$, among $H_A H$, $E_A H$, and fluorene, $E_A H$ has the highest electron affinity and $H_A H$ has the smallest ionization potential. In addition, in the formula, the 1- to 8-positions of fluorene may have substituents. As the substituents, either an alkyl group having 1 to 6 carbon atoms or an aryl group having 6 to 13 carbon atoms can be selected.

<Synthesis Method 1>

First, a halide of the electron-accepting unit $E_A$ (Compound 1) and an acyl compound of the hole-accepting unit $H_A$ (Compound 2) are reacted with each other, whereby Compound 3 having a ketone structure is obtained (Reaction Formula (A-1-1).

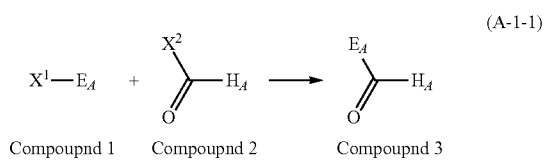

(A-1-1)

Note that in Reaction Formula (A-1-1), $X^1$ represents a substituent which increases the nucleophilicity of bonded carbon (to the level that carbon of a carboxyl group can be nucleophilically attacked), such as magnesium bromide (Grignard reagent) or lithium, and $X^2$ represents halogen, an alkoxy group, a hydroxyl group, hydrogen, or the like.

Compound 3 can also be obtained by reaction represented by Reaction Formula (A-1-2) below. In Reaction Formula (A-1-2) below, a halide of the hole-accepting unit $H_A$ (Compound 4) and an acyl compound of the electron-accepting unit $E_A$ (Compound 5) are reacted with each other, whereby Compound 3 having a ketone structure is obtained.

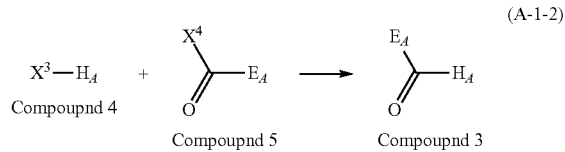

(A-1-2)

Note that in Reaction Formula (A-1-2), $X^3$ represents a substituent which increases the nucleophilicity of bonded carbon (to the level that carbon of a carboxyl group can be nucleophilically attacked), such as magnesium bromide (Grignard reagent) or lithium, and $X^4$ represents halogen, alkoxy group, a hydroxyl group, hydrogen, or the like.

Then, a biphenyl derivative (Compound 6) and Compound 3 are reacted with each other, whereby an alcohol (Compound 7) can be obtained (Reaction Formula (A-2)).

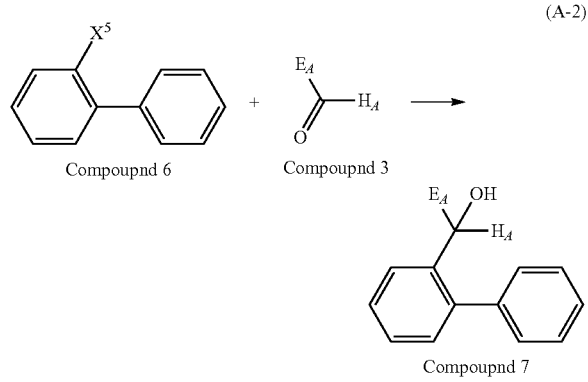

(A-2)

Note that in Reaction Formula (A-2), $X^5$ represents a substituent which increases the nucleophilicity of bonded carbon (to the level that carbon nucleophilic such as a carboxyl group can be attacked), such as magnesium bromide (Grignard reagent) or lithium.

Lastly, Compound 7 is subjected to cyclodehydration reaction, whereby the organic semiconductor material represented by General Formula (G1) which is an objective substance of the synthesis can be obtained (Reaction Formula (A-3)).

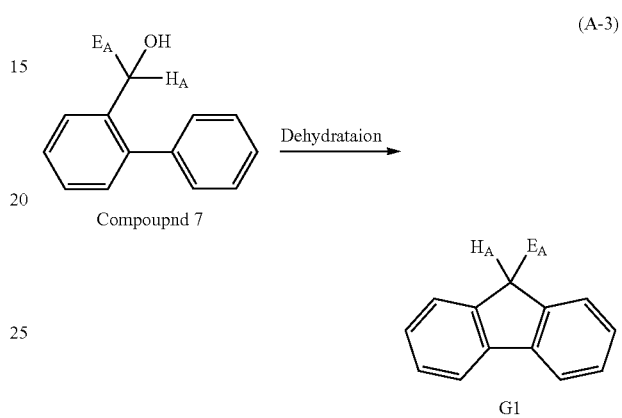

(A-3)

As examples of a dehydrating agent that can be used in Reaction Formula (A-3), an acid catalyst such as hydrochloric acid or sulfuric acid, and the like are given.

Next, another synthesis method of the compound (G1) will be described.

<Synthesis Method 2>

In Synthesis Method 2, the hole-accepting unit $H_A$, which is bonded to the 9-position of fluorene of the organic semiconductor material represented by General Formula (G1) which is described in Embodiment 1, is represented as an $H_A^1$—$R^1$-group using a hole-transport skeleton $H_A^1$ and an arylene group $R^1$. Accordingly, the organic semiconductor material represented by General Formmula (G1) can be represented by General Formula (G1-1) below.

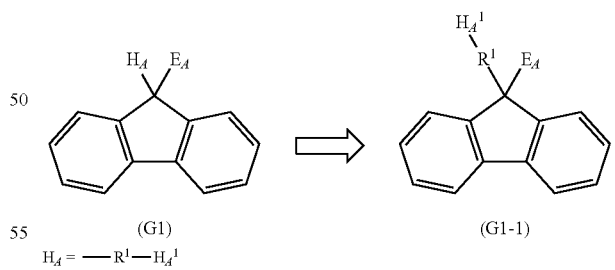

(G1)          (G1-1)

$H_A =$ —$R^1$—$H_A^1$

Note that in the Synthesis Method 2, as examples of the substituent represented by the hole-accepting skeleton $H_A^1$, a π-electron rich heteroaromatic substituent, a diarylamino group, and the like are given. In addition, $R^1$ represents an arylene group.

First, the halide of the electron-accepting unit $E_A$ (Compound 1) and an acyl compound (Compound 8) are reacted with each other, whereby Compound 9 having a ketone structure can be obtained (Reaction Formula (B-1).

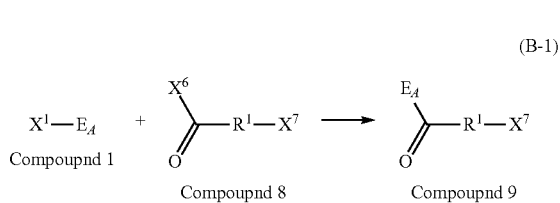

(B-1)

Note that in Reaction Formula (B-1), $X^1$ represents a substituent which increases the nucleophilicity of bonded carbon (to the level that carbon of a carboxyl group can be nucleophilically attacked), such as magnesium bromide (Grignard reagent) or lithium, $X^6$ represents halogen, an alkoxy group, a hydroxyl group, hydrogen, or the like, and $X^7$ represents halogen, a hydroxyl group, or the like.

Then, a biphenyl derivative (Compound 6) and Compound 9 are reacted with each other, whereby an alcohol (Compound 7) can be obtained (Reaction Formula (B-2)).

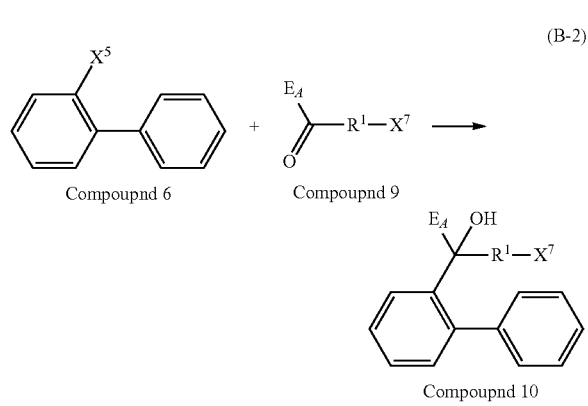

(B-2)

In Reaction Formula (B-2), $X^5$ represents a substituent which increases the nucleophilicity of bonded carbon (to the level that carbon of a carboxyl group can be nucleophilically attacked), such as magnesium bromide (Grignard reagent) or lithium, and $X^7$ represents halogen, a hydroxyl group, or the like.

Then, Compound 10 is subjected to cyclodehydration reaction, whereby a fluorene compound (Compound 11) can be obtained (Reaction Formula (B-3)).

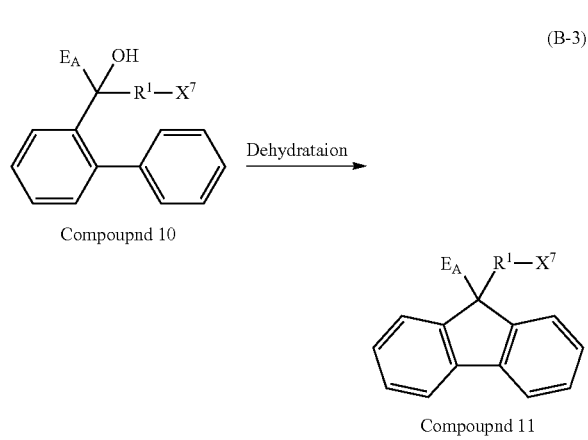

(B-3)

As examples of a dehydrating agent that can be used in Reaction Formula (B-3), an acid catalyst such as hydrochloric acid or sulfuric acid, and the like are given.

Lastly, coupling reaction of Compound 11 and Compound 12 having the hole-accepting skeleton $H_A{}^1$ is performed, whereby the organic semiconductor material represented by General Formula (G1-1) which is an objective substance of the synthesis can be obtained (Reaction Formula (B-4)).

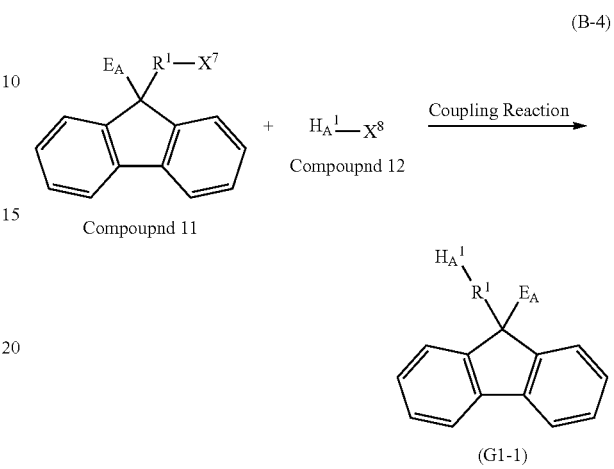

(B-4)

(G1-1)

In Reaction Formula (B-4), $X^7$ represents halogen or a triflate group (synthesized from a hydroxyl group), $X^8$ represents boronic acid (boronic acid may have a structure protected by ethylene glycol or the like) or the like. As an example of the coupling reaction in Reaction Formula (B-4), the Suzuki-Miyaura coupling using a palladium catalyst, or the like is given.

Next, another synthesis method of the compound (G1) will be described.

<Synthesis Method 3>

In Synthesis Method 3, the electron-accepting unit $E_A$, which is bonded to the 9-position of fluorene of the organic semiconductor material represented by General Formula (G1) which is described in Embodiment 1, is represented as an $E_A{}^1$-$R^2$-group using an electron-transport skeleton $E_A{}^1$ and an arylene group $R^2$. Accordingly, the organic semiconductor material represented by General Formula (G1) can be represented by General Formula (G1-2) below.

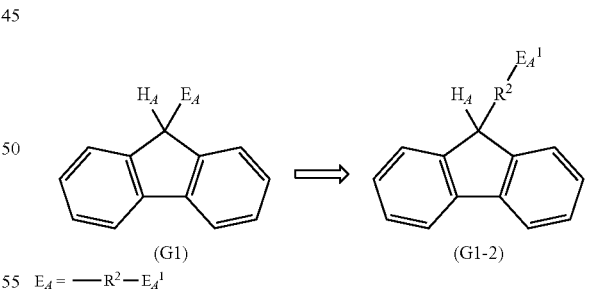

$E_A = \text{—} R^2 \text{—} E_A{}^1$

In Synthesis Method 3, as examples of the substituent represented by $E_A{}^1$, a nitrogen-containing 6-membered aromatic ring, a 1,2-azole group, a 1,3-azole group, a polyazole group, and the like are given. In addition, $R^2$ represents an arylene group.

First, a halide of the hole-accepting unit $H_A$ (Compound 4) and an acyl compound (Compound 13) having $R^2$ are reacted with each other, whereby Compound 14 including a hole-accepting unit $H_A$ and $R^2$ and having a ketone structure can be obtained (Reaction Formula (C-1).

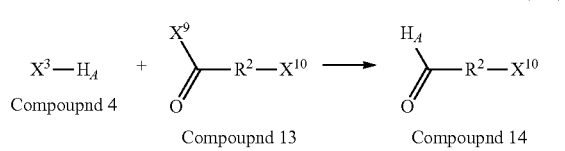

(C-1)

Note that in Reaction Formula (C-1), $X^3$ represents a substituent which increases the nucleophilicity of bonded carbon (to the level that carbon of a carboxyl group can be nucleophilically attacked), such as magnesium bromide (Grignard reagent) or lithium, $X^9$ represents halogen, an alkoxy group, a hydroxyl group, hydrogen, or the like, and $X^{10}$ represents halogen, a hydroxyl group, or the like.

Then, a biphenyl derivative (Compound 6) and Compound 14 are reacted with each other, whereby an alcohol (Compound 15) can be obtained (Reaction Formula (C-2)).

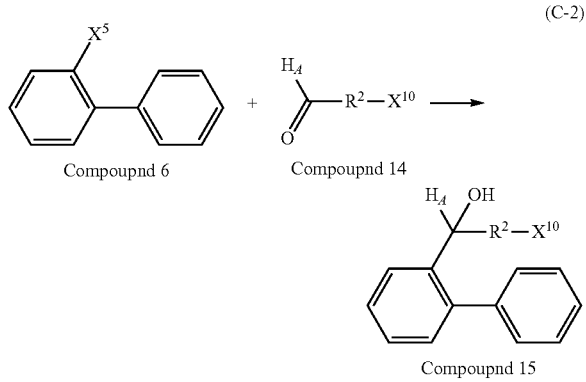

(C-2)

In Reaction Formula (C-2), $X^5$ represents a substituent which increases the nucleophilicity of bonded carbon (to the level that carbon of a carboxyl group can be nucleophilically attacked), such as magnesium bromide (Grignard reagent) or lithium, and $X^{10}$ represents halogen, a hydroxyl group, or the like.

Then, Compound 15 is subjected to cyclodehydration reaction, whereby Compound 16 can be obtained (Reaction Formula (C-3)).

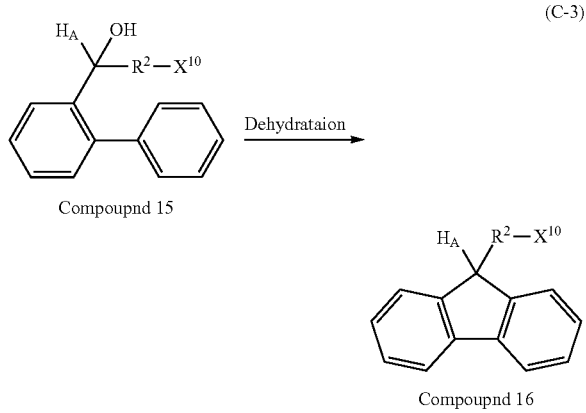

(C-3)

As examples of a dehydrating agent that can be used in Reaction Formula (C-3), an acid catalyst such as hydrochloric acid or sulfuric acid, and the like are given. In Reaction Formula (C-3), $X^{10}$ represents halogen, a hydroxyl group, or the like.

Lastly, coupling reaction of Compound 16 and Compound 17 having the electron-accepting gkeleton $E_A^1$ is performed, whereby the organic semiconductor material represented by General Formula (G1-2) which is an objective substance of the synthesis can be obtained (Reaction Formula (C-4)).

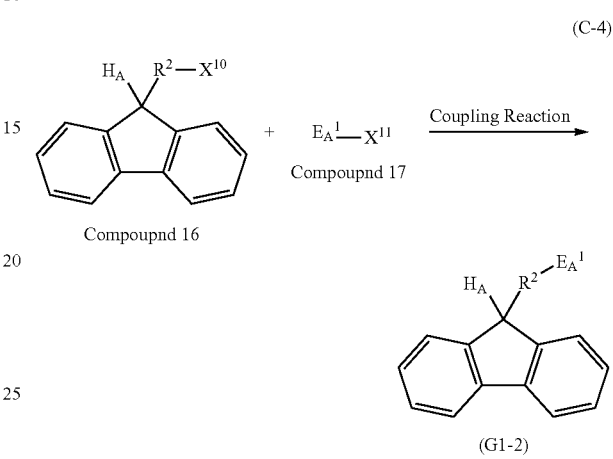

(C-4)

In Reaction Formula (C-4), $X^{10}$ represents halogen or a triflate group (synthesized with a hydroxyl group), $X^{11}$ represents boronic acid (boronic acid may have a structure protected by ethylene glycol or the like) or the like. As an example of the coupling reaction in Reaction Formula (C-4), the Suzuki-Miyaura coupling using a palladium catalyst, or the like is given.

Further, another synthesis method of the compound (G1) will be described.

<Synthesis Method 4>

In Synthesis Method 4, the hole-accepting unit $H_A$, which is bonded to the 9-position of fluorene of the organic semiconductor material represented by General Formula (G1) which is described in Embodiment 1, is represented as an $H_A^1$—$R^1$-group using a hole-transport skeleton $H_A^1$ and an arylene group $R^1$; and the electron-accepting unit $E_A$ is represented as an $E_A^1$-$R^2$ group using an electron-transport skeleton $E_A^1$ and an arylene group $R^2$. Accordingly, the organic semiconductor material represented by General Formula (G1) can be represented by General Formula (G1-3) below.

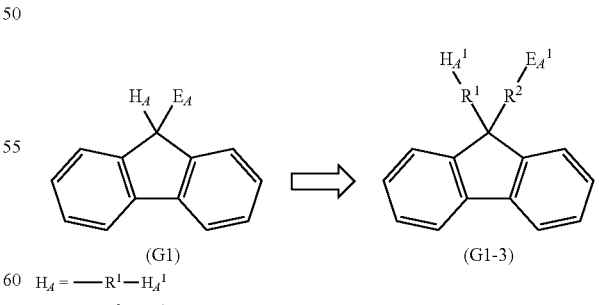

$H_A = $ —$R^1$—$H_A^1$ $E_A = $ —$R^2$—$E_A^1$

In Synthesis Method 4, as examples of the substituent represented as the electron-transport skeleton $E_A^1$, a nitrogen-containing 6-membered aromatic ring, a 1,2-azole group, a 1,3-azole group, a polyazole group, and the like are given. As examples of the substituent represented as the hole-transport skeleton $H_A^1$, a π-electron rich heteroaromatic substituent, a diarylamino group, and the like are given. In addition, $R^1$ and $R^2$ represent an arylene group.

First, the biphenyl derivative (Compound 6) and Compound 18 including $R^1$ and $R^2$ and having a ketone structure are reacted with each other, whereby an alcohol (Compound 19) can be obtained (Reaction Formula (D-1)).

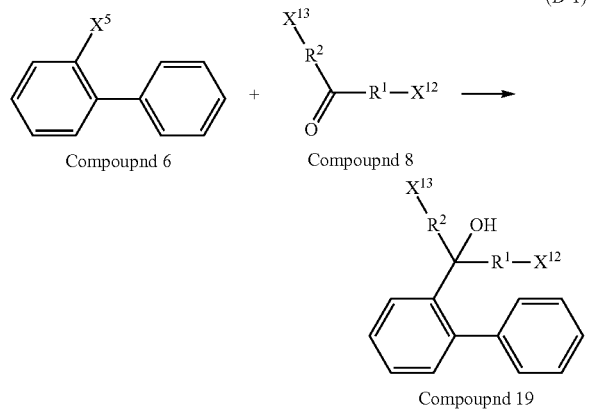

Note that in Reaction Formula (D-1), $X^5$ represents a substituent which increases the nucleophilicity of bonded carbon (to the level that carbon of a carboxyl group can be nucleophilically attacked), such as magnesium bromide (Grignard reagent) or lithium, $X^{12}$ and $X^{13}$ represent halogen, a hydroxyl group, or the like.

Then, Compound 19 is subjected to cyclodehydration reaction, whereby a fluorene compound (Compound 20) can be obtained (Reaction Formula (D-2)).

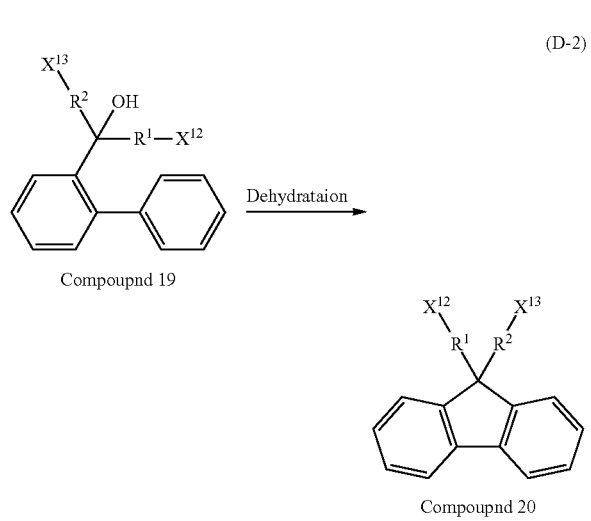

As examples of a dehydrating agent that can be used in Reaction Formula (D-2), an acid catalyst such as hydrochloric acid or sulfuric acid, and the like are given.

In Reaction Formula (D-2), $X^{12}$ and $X^{13}$ separately represent halogen, a hydroxyl group, or the like.

Then, coupling reaction of Compound 20 and Compound 12 having the hole-accepting skeleton $H_A^1$ is performed, whereby Compound 21 can be obtained (Reaction Formula (D-3-1)).

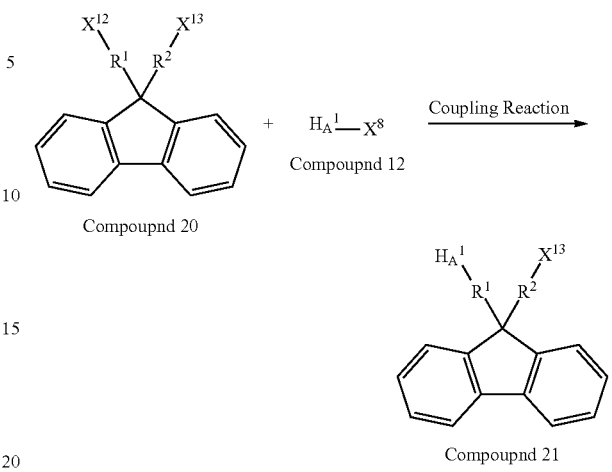

In Reaction Formula (D-3-1), $X^{12}$ and $X^{13}$ represent halogen or a triflate group (synthesized with a hydroxyl group), $X^8$ represents boronic acid (boronic acid may have a structure protected by ethylene glycol or the like) or the like. $X^{12}$ and $X^{13}$ may be the same as or different from each other. As an example of the coupling reaction in Reaction Formula (D-3-1), the Suzuki-Miyaura coupling using a palladium catalyst, or the like is given.

Lastly, coupling reaction of Compound 21 and Compound 17 having the electron-accepting skeleton $E_A^1$ is performed, whereby the organic semiconductor material represented by General Formula (G1-3) which is an objective substance of the synthesis can be obtained (Reaction Formula (D-3-2)).

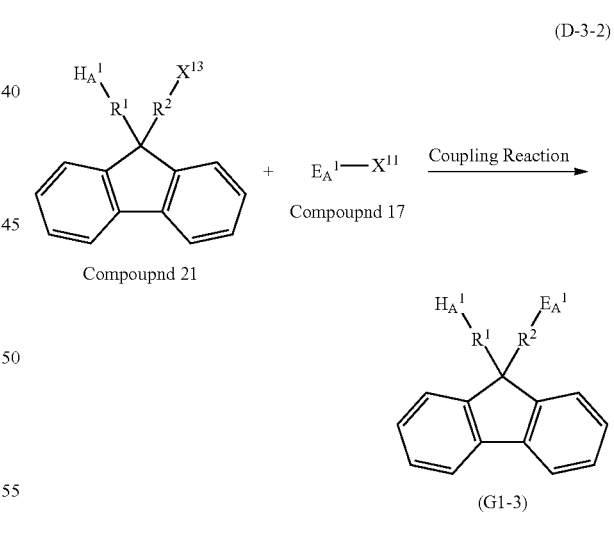

In Reaction Formula (D-3-2), $X^{13}$ represents halogen or a triflate group (synthesized with a hydroxyl group), $X^{11}$ represents boronic acid (boronic acid may have a structure protected by ethylene glycol or the like) or the like. As an example of the coupling reaction in Reaction Formula (D-3-2), the Suzuki-Miyaura coupling using a palladium catalyst, or the like is given.

In Synthesis Method 4, Compound 17 having the electron-accepting skeleton $E_A^1$ may be firstly coupled with Compound 20. In other words, coupling of Compound 17 having the electron-accepting skeleton $E_A^1$ and Compound 20 is firstly performed to obtain Compound 22 (Reaction Formula (D-4-1)).

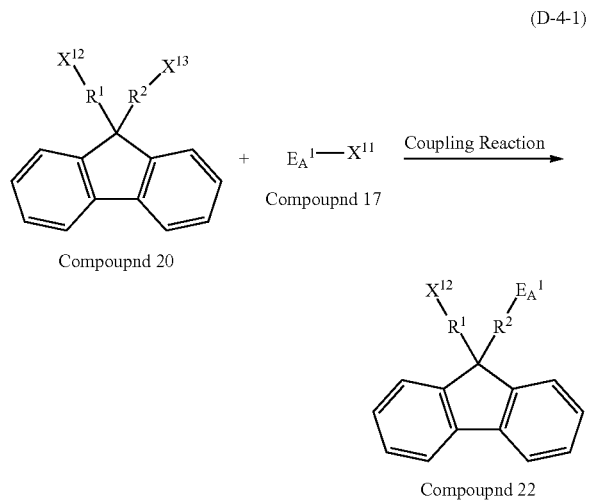

In Reaction Formula (D-4-1), $X^{12}$ and $X^{13}$ represent halogen or a triflate group (synthesized with a hydroxyl group), $X^{11}$ represents boronic acid (boronic acid may have a structure protected by ethylene glycol or the like) or the like. $X^{12}$ and $X^{13}$ may be the same as or different from each other. As an example of the coupling reaction in Reaction Formula (D-4-1), the Suzuki-Miyaura coupling using a palladium catalyst, or the like is given.

Lastly, coupling reaction of Compound 22 and Compound 12 having the hole-accepting skeleton $H_A^1$ is performed, whereby the organic semiconductor material represented by General Formula (G1-3) which is an objective substance of the synthesis can be obtained (Reaction Formula (D-4-2)).

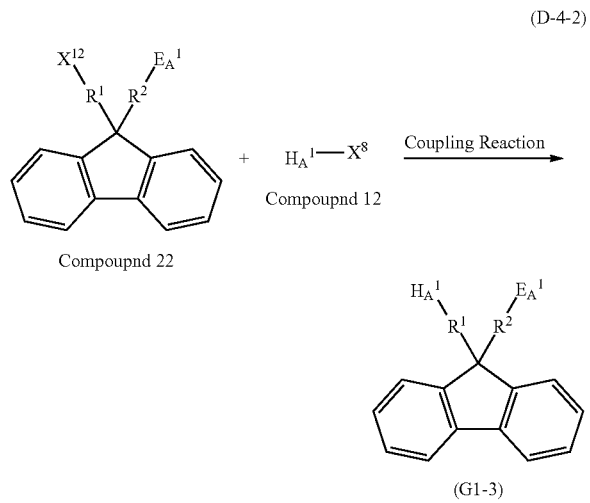

In Reaction Formula (D-4-2), $X^{12}$ represents halogen or a triflate group (synthesized with a hydroxyl group) and $X^8$ represents boronic acid (boronic acid may have a structure protected by ethylene glycol or the like) or the like. As an example of the coupling reaction in Reaction Formula (D-4-2), the Suzuki-Miyaura coupling using a palladium catalyst, or the like is given.

By the synthesis methods described above, the organic semiconductor material represented by General Formula (G1) which is the organic semiconductor material described in Embodiment 1 can be synthesized.

Note that in Synthesis Methods 1 to 3, a disubstituted compound having only the electron-accepting unit $E_A$ or only the hole-transport unit $H_A$ is not generated, which makes it possible to easily perforin purification. Therefore, it can be said that Synthesis Methods 1 to 3 are very effective in introducing two different units (an electron-accepting unit and a hole-accepting unit) to the 9-position of fluorene.

Embodiment 3

In this embodiment, one embodiment of a light-emitting element including the organic semiconductor material described in Embodiment 1 will be described with reference to FIG. 1 and FIG. 2.

The light-emitting element of the present invention includes a plurality of layers between a pair of electrodes. The plurality of layers is a combination of a layer containing a substance having a high carrier-injection property and a layer containing a substance having a high carrier-transport property which are stacked so that a light-emitting region is formed in a region away from the electrodes, that is, so that carriers recombine in a region away from the electrodes.

In this embodiment, the light-emitting element includes a first electrode 102, a second electrode 104, and an EL layer 103 provided between the first electrode 102 and the second electrode 104. Note that in this embodiment, description is made on the assumption that the first electrode 102 functions as an anode and that the second electrode 104 functions as a cathode. In other words, the description will be made below on the assumption that light emission can be obtained when voltage is applied between the first electrode 102 and the second electrode 104 so that the potential of the first electrode 102 is higher than that of the second electrode 104.

The substrate 101 is used as a support of the light-emitting element. The substrate 101 can be formed of, for example, glass, plastic, metal, or the like. Note that the substrate 101 may be made of materials other than glass or plastic as long as it can function as a support of the light-emitting element. Note that in the case where light emitted from the light-emitting element is extracted outside through the substrate 101, the substrate 101 is preferably a light-transmitting substrate.

The first electrode 102 is preferably formed using any of metals, alloys, or conductive compounds, a mixture thereof, or the like with a high work function (specifically, a work function of greater than or equal to 4.0 eV is preferable). For example, indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), and the like are given. Such a conductive metal oxide film is generally formed by a sputtering method, but may also be formed by an ink-jet method, a spin coating method, or the like by application of a sol-gel method or the like. For example, indium oxide-zinc oxide (IZO) can be formed by a sputtering method using indium oxide into which 1 wt % to 20 wt % of zinc oxide is added, as a target. Moreover, indium oxide (IWZO) containing tungsten oxide and zinc oxide can be formed by a sputtering method using a target in which 0.5 wt % to 5 wt % of tungsten oxide and 0.1 wt % to 1 wt % of zinc oxide with respect to indium oxide are included. Besides, gold (Au), platinum (Pt), nickel (Ni), tungsten (W), chromium (Cr), molybdenum (Mo), iron (Fe), cobalt (Co), copper (Cu), palladium (Pd), titanium (Ti), nitrides of the metal materials (such as titanium nitride: TiN), and the like are given. Graphene can also be used.

In the case where a layer containing a composite material described below is used as a layer in contact with the first electrode 102, various metals, alloys, electrically conductive compounds, or a mixture thereof can be used for the first electrode 102 regardless of the work function. For example, aluminum (Al), silver (Ag), an aluminum alloy (AlSi), or the like can be used. Besides, an element that belongs to Group 1 or Group 2 of the periodic table which has a low work function, i.e., alkali metals such lithium (Li) and cesium (Cs) and alkaline earth metals such as magnesium (Mg), calcium (Ca), and strontium (Sr); alloys of them (e.g., MgAg and AlLi); rare earth metals such as europium (Eu) and ytterbium (Yb); alloys of them; and the like can be used. A film of an alkali metal, an alkaline earth metal, or an alloy containing these metals can be formed by a vacuum evaporation method. An alloy containing an alkali metal or an alkaline earth metal can be formed by a sputtering method. Further, a silver paste or the like can be formed by an ink-jet method or the like.

The EL layer 103 described in this embodiment includes a hole-injection layer 111, a hole-transport layer 112, a light-emitting layer 113, an electron-transport layer 114, and an electron-injection layer 115. As long as the EL layer 103 includes at least a light-emitting layer, there is no particular limitation on the structure of the other stacked layers. In other words, there is no particular limitation on the stacked structure of layers of the EL layer 103; layers formed of a substance having a high electron-transport property, a substance having a high hole-transport property, a substance having a high electron-injection property, a substance having a high hole-injection property, a bipolar substance (a substance having high electron-transport and hole-transport properties), a substance having a high light-emitting property may be combined with the organic semiconductor material described in Embodiment 1 as appropriate to form the EL layer 103. For example, the EL layer 103 may be formed by any combination of a hole-injection layer, a hole-transport layer, a light-emitting layer, an electron-transport layer, an electron-injection layer, and the like, as appropriate. Materials for forming layers will be specifically given below.

The hole-injection layer 111 is a layer that contains a substance having a high hole-injection property. As a substance having a high hole-injection property, molybdenum oxide, vanadium oxide, ruthenium oxide, tungsten oxide, manganese oxide, or the like can be used. Besides, as a low molecular organic compound, the following compounds are given: phthalocyanine-based compounds such as phthalocyanine ($H_2Pc$), copper(II) phthalocyanine (CuPc), and vanadyl phthalocyanine (VOPc); aromatic amine compounds such as 4,4',4''-tris(N,N-diphenylamino)triphenylamine 0 (TDATA), 4,4',4''-tris[N-(3-methylphenyl)-N-phenylamino]triphenylamine (MTDATA), 4,4'-bis[N-(4-diphenylaminophenyl)-N-phenylamino]biphenyl (DPAB), 4,4'-bis(N-{4-[N'-(3-methylphenyl)-N'-phenylamino]phenyl}-N-phenylamino) biphenyl (DNTPD), 1,3,5-tris[N-(4-diphenylaminophenyl)-N-phenylamino]benzene (DPA3B), 3-[N-(9-phenylcarbazol-3-yl)-N-phenylamino]-9-phenylcarbazole (PCzPCA1), 3,6-bis[N-(9-phenylcarbazol-3-yl)-N-phenylamino]-9-phenylcarbazole (PCzPCA2), and 3-[N-(1-naphthyl)-N-(9-phenylcarbazol-3-yl)amino]-9-phenylcarbazole (PCzPCN1), and the like.

Alternatively, for the hole-injection layer 111, a composite material in which an acceptor substance is mixed into a substance having a high hole-transport property can be used. Note that when a material formed by mixing an acceptor substance into a substance with a high hole-transport property is used, materials for forming the electrode can be selected regardless of the work function. In other words, besides a material with a high work function, a material with a low work function may also be used as the first electrode 102. Such a composite material can be formed by co-deposition of a substance with a high hole-transport property and an acceptor substance.

Note that, in this specification, "composition" means not only a simple mixture of two materials but also a mixture of a plurality of materials in a condition where an electric charge is given and received among the materials.

As the organic compound used for the composite material, various compounds such as an aromatic amine compound, carbazole derivatives, aromatic hydrocarbon, and a high molecular compound (such as oligomer, dendrimer, or polymer) can be used. Note that the organic compound used for the composite material is preferably an organic compound having a high hole-transport property. Specifically, a substance having a hole mobility of higher than or equal to $10^{-6}$ $cm^2/Vs$ is preferably used. Note that any substance other than the above substances may also be used as long as they are substances whose hole-transport property is higher than the electron-transport property. Examples of the organic compound which can be used for the composite material are specifically given below.

As examples of the organic compound used for the composite material, the following are given: aromatic amine compounds such as MTDATA, TDATA, DPAB, DNTPD, DPA3B, PCzPCA1, PCzPCA2, PCzPCN1, 4,4'-bis[N-(1-naphthyl)-N-phenylamino]biphenyl (abbreviation: NPS or α-NPD), and $N,N^1$-bis(3-methylphenyl)-N,N'-diphenyl-[1,1'-biphenyl]-4,4'-diamine (abbreviation: TPD); carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene; and aromatic hydrocarbon compounds such as 2-tert-butyl-9,10-di(2-naphthyl)anthracene (abbreviation: t-BuDNA), 2-tert-butyl-9,10-di(1-naphthyl) anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl) anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl) anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl) phenyl]anthracene (abbreviation: DPVPA).

As examples of the acceptor substance, organic compounds such as 7,7,8,8-tetracyano-2,3,5,6-tetrafluoroquinodimethane (abbreviation: $F_4$-TCNQ) and chloranil, and a transition metal oxide can be given. In addition, oxides of metals that belongs to Groups 4 to 8 in the periodic table can be given. Specifically, vanadium oxide, niobium oxide, tantalum oxide, chromium oxide, molybdenum oxide, tungsten oxide, manganese oxide, and rhenium oxide are preferable since their electron-accepting property is high. Among those, molybdenum oxide is especially preferable since it is stable in the air, has a low hygroscopic property, and is easily handled.

For the hole-injection layer 111, a high molecular compound (oligomer, dendrimer, polymer, or the like) can be used. As examples of the high molecular compound, the following are given: poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N-phenylamino}phenyl)methacrylamide] (abbreviation: PTPDMA), and poly[N,N'-bis(4-butylphenyl)-N,N'-bis(phenyl)benzidine (abbreviation: poly-TPD).

Alternatively, a high molecular compound to which acid is added, such as poly(3,4-ethylenedioxythiophene)/poly(styrenesulfonic acid) (PEDOT/PSS), or polyaniline/poly(styrenesulfonic acid) (PAni/PSS), can be used.

Note that the hole-injection layer 111 can be formed using a composite material of the above high molecular compound, such as PVK, PVTPA, PTPDMA, or Poly-TPD, and the above acceptor substance.

The hole-transport layer 112 is a layer that contains a substance having a high hole-transport property. As the substance having a high hole-transport property, the following low molecular organic compound can be used: an aromatic amine compound such as NPB (or a-NPD), TPD, 4,4'-bis[N-(9,9-dimethylfluoren-2-yl)-N-phenylamino]biphenyl (DFLDPBi), or 4,4'-bis[N-(spiro-9,9'-bifluoren-2-yl)-N-phenylamino]-biphenyl (BSPB); 4,4',4"-tris[N-(3-methylphenyl)-N-phenylamino]triphenylamine (m-MTDATA); N-[4-(9H-carbazol-9-yl)phenyl]-N-phenyl-spiro-9,9'-bifluoren-2-amine (YGASF), N,N'-bis[4-(9H-carbazol-9-yl)phenyl-N,N'-diphenylvinyl-4,4'-diamine (YGABP); 4-(9H-carbazol-9-yl)-2'-phenyltriphenylamine (o-YGA1BP); 4-(9H-carbazol-9-yl)-3'-phenyltriphenylamine (m-YGA1BP); 4-(9H-carbazol-9-yl)-4'-phenyltriphenylamine (p-YGA1BP); 1,3,5-tris(N-carbazolyl)benzene (TCzB); or 4,4',4"-tris(N-carbazolyl)triphenylamine (TCTA). The substances given here are mainly substances each having an electron mobility of higher than or equal to $10^{-6}$ cm$^2$/Vs. Note that any substance other than the above substances may also be used as long as they are substances whose hole-transport property is higher than the electron-transport property. Note that the layer containing a substance having a high hole-transport property is not limited to a single layer, and may include two or more layers containing any of the above materials may also be stacked.

Furthermore, for the hole-transport layer 112, a composite material in which an acceptor substance is contained in the above substance having a high hole-transport property can be used.

For the hole-transport layer 112, a high molecular compound such as PVK, PVTPA, PTPDMA, or Poly-TPD can be used.

The light-emitting layer 113 is a layer that contains a substance having a high light-emitting property, and can be formed using various materials for the light-emitting layer 113. As the substance with a high light-emitting property, for example, a fluorescent compound which emits fluorescence or a phosphorescent compound which emits phosphorescence can be used. Plural kinds of substances having a high light-emitting property may be used without limitation to one type.

As the phosphorescent compound that can be used for the light-emitting layer, a material for blue light emission, a material for green light emission, a material for yellow light emission, a material for orange light emission, and a material for red light emission are given. As examples of the material for blue light emission, the following are given: bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis[2-(3',5' bistrifluoromethylphenyl)pyridinato-N,C$^{2'}$]iridium(III) picolinate (abbreviation: Ir(CF$_3$ppy)$_2$(pic)), bis[2-(4',6'-difluorophenyl)pyridinato-N,C$^{2'}$]iridium(III) acetylacetonate (abbreviation: FIr(acac)), and the like. As examples of the material for green light emission, the following are given: tris(2-phenylpyridinato-N,C$^{2'}$)iridium(III) (abbreviation: Ir(ppy)$_3$), bis[2-phenylpyridinato-N, C$^{2'}$]iridium(III) acetylacetonate (abbreviation: Ir(ppy)$_2$(acac)), bis(1,2-diphenyl-1H-benzimidazolato)iridium(III) acetylacetonate (abbreviation: Ir(pbi)$_2$(acac)), bis(benzo[h]quinolinato)iridium(III)acetylacetonate (abbreviation: Ir(bzq)$_2$(acac)), and the like. As examples of the material for yellow light emission, the following are given: bis(2,4-diphenyl-1,3-oxazolato-N,C$^{2'}$)iridium(III)acetylacetonate (abbreviation: Ir(dpo)$_2$(acac)), bis[2-(4'-perfluorophenylphenyl)pyridinato]iridium(III)acetylacetonate (abbreviation: Ir(p-PF-ph)$_2$(acac)), bis(2-phenylbenzothiazolato-N,C$^{2'}$)iridium(III)acetylacetonate (abbreviation: Ir(bt)$_2$(acac)), and the like. As examples of the material for orange light emission, the following are given: tris(2-phenylquinolinato-N,C$^{2'}$)iridium(III) (abbreviation: Ir(pq)$_3$), bis(2-phenylquinolinato-N,C$^{2'}$)iridium(III)acetylacetonate (abbreviation: Ir(pq)$_2$(acac)), and the like. As examples of the material for red light emission, organometallic complexes such as bis[2-(2'-benzo[4,5-a]thienyl)pyridinato-N,C$^{3'}$]iridium(III) acetylacetonate (abbreviation: Ir(btp)$_2$(acac)), bis(1-phenylisoquinolinato-N,C$^{2'}$)iridium(III)acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), 2,3,7,8,12,13,17,18-octaethyl-21H,23H-porphyrinatoplatinum(II) (abbreviation: PtOEP), and the like are given. In addition, rare-earth metal complexes, such as tris(acetylacetonato)(monophenanthroline)terbium(III) (abbreviation: Tb(acac)$_3$(Phen)), tris(1,3-diphenyl-1,3-propanedionato)(monophenanthroline)europium(III) (abbreviation: Eu(DBM)$_3$(Phen)), and tris[1-(2-thenoyl)-3,3,3-trifluoroacetonato](monophenanthroline)europium(III) (abbreviation: Eu(TTA)$_3$(Phen)), exhibit light emission from rare-earth metal ions (electron transition between different multiplicities), and thus can be used as phosphorescent compounds.

As the fluorescent compound that can be used for the light-emitting layer, a material for blue light emission, a material for green light emission, a material for yellow light emission, and a material for red light emission are given. As examples of the material for blue light emission, the following are given: N,N'-bis[4-(9H-carbazol-9-yl)phenyl]-N,N'-diphenylstilbene-4,4'-diamine (abbreviation: YGA2S),4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene; 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), and the like. As examples of the material for green light emission, the following are given: N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. As examples of the material for yellow light emission, rubrene, 5,12-bis(1,1'-biphenyl-4-yl)-6,11-diphenyltetracene (abbreviation: BPT), and the like are given. As examples of the material for red light emission, N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-d iamine (abbreviation: p-mPhAFD), and the like are given.

Note that the light-emitting layer may have a structure in which any of the above substances having a high light-emitting property (guest material) is dispersed into another substance (host material). A variety of types of substances can be used for a material for dispersing the light-emitting substance (host material), and it is preferable to use a substance whose lowest unoccupied molecular orbital (LUMO) level is higher than that of a substance having a high light-emitting property (guest material) and whose highest occupied molecular orbital (HOMO) level is lower than that of the substance having a high light-emitting property (guest material). Note that in this specification, "the HOMO level or the LUMO level is high" means that the energy level is high, while "the HOMO level or the LUMO level is low" means that the energy level is low. For example, supposing that a substance A has a HOMO level of −5.5 eV, a substance B has a HOMO level of −5.2 eV, and a substance C has a HOMO level of −5.7 eV, the HOMO level of the substance A is 0.3 eV lower than that of the substance B and 0.2 eV higher than that of the substance C.

The organic semiconductor material described in Embodiment 1 has a large band gap and a bipolar property, and thus is suitable as a host material. The organic semiconductor material described in Embodiment 1 has a large band gap; thus, light emission from a guest material can be efficiently obtained even in the case where a guest material which exhibits light emission with a short wavelength is used. In addition, the driving voltage of the light-emitting element can be reduced.

Further, the organic semiconductor material described in Embodiment 1 has high triplet excitation energy; thus, light emission from a guest material can be efficiently obtained even in the case where a phosphorescent compound is used as a guest material. Especially in the case where a phosphorescent compound which exhibits light emission with a short wavelength is used, a prominent effect can be obtained.

Plural types of materials can be used as the host materials. For example, in order to suppress crystallization, a substance such as rubrene which suppresses crystallization, may be further added. In addition, NPB, Alq, or the like may be further added in order to efficiently transfer energy to the light-emissive substance.

The structure in which a substance having a high light-emitting property (guest material) is dispersed in another substance (host material) is used for the light-emitting layer, whereby crystallization of the light-emitting layer 113 can be suppressed. In addition, concentration quenching due to the increase in concentration of the substance having a high light-emitting property (guest material) can also be suppressed.

The electron-transport layer 114 is a layer that contains a substance having a high electron-transport property. For example, as a low molecular organic compound, metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]quinolinato)beryilium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ) can be used. Further, the following heterocyclic compounds can be also used: 2-(4-biphenylyl)-5-(4-tert-butylphenyl)-1,3,4-oxadiazole (abbreviation: PBD); 1,3-bis[5-(p-tert-butylphenyl)-1,3,4-oxadiazol-2-yl]benzene (abbreviation: OXD-7); 3-(4-biphenylyl)-4-phenyl-5-(4-tert-butylphenyl)-1,2,4-triazole (abbreviation: TAZ01); 2,2',2"-(1,3,5-benzenetriyl)-tris(1-phenyl-1H-benzimidazole) (abbreviation: TPBI); bathophenanthroline (abbreviation: BPhen); bathocuproine (abbreviation: BCP); and the like. The substances given here are mainly substances each having an electron mobility of higher than or equal to $10^{-6}$ cm$^2$/Vs. Note that the electron-transport layer 114 may be formed using substances other than those described above as long as they are substances whose electron-transport property is higher than the hole-transport property. Note that the electron-transport layer is not limited to a single layer, and two or more layers formed using any of the substances may be stacked.

For the electron-transport layer 114, a high molecular compound can be used. For example, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy), or the like can be used.

The electron-injection layer 115 is a layer that contains a substance having a high electron-injection property. As the substance having a high electron-injection property, an alkali metal, an alkaline-earth metal or a compound thereof such as lithium (Li), magnesium (Mg), lithium fluoride (LiF), cesium fluoride (CsF), or calcium fluoride (CaF$_2$) can be used. For example, a layer of a material having an electron-transport property containing an alkali metal, an alkaline earth metal, or a compound thereof, such as Alq which contains magnesium (Mg), can be used. Note that a layer of a substance having an electron-transport property to which an alkali metal or an alkaline earth metal is added is preferably used as the electron-injection layer, in which case electron injection from the second electrode 104 is performed efficiently.

As a substance for forming the second electrode 104, a metal, an alloy, an electrically conductive compound, a mixture thereof, or the like with a low work function (specifically, a work function of lower than or equal to 3.8 eV is preferable) can be used. As typical examples of such a cathode material, an element that belongs to Group 1 or Group 2 of the periodic table, i.e., an alkali metal such as lithium (Li) or cesium (Cs), or an alkaline earth metal such as magnesium (Mg), calcium (Ca), or strontium (Sr); an alloy containing any of these (such as MgAg or AlLi); a rare earth metal such as europium (Eu) or ytterbium (Yb); an alloy containing such a rare earth metal; and the like are given. A film of an alkali metal, an alkaline earth metal, or an alloy including these can be formed by a vacuum evaporation method. Alternatively, an alloy containing an alkali metal or an alkaline earth metal can be formed by a sputtering method. Further, a silver paste or the like can be formed by an ink-jet method or the like.

Further, by providing the electron-injection layer 115 which is a layer having a function of promoting injection of electrons between the second electrode 104 and the electron-transport layer 114, the second electrode 104 can be formed using any of a variety of conductive materials such as Al, Ag, ITO, or indium oxide-tin oxide containing silicon or silicon oxide, regardless of the work functions. Films of these conductive materials can be formed by a sputtering method, an ink-jet method, a spin coating method, or the like.

Note that the organic semiconductor material described in Embodiment 1 exhibits light emission, in which case it can be used as a substance having a high light-emitting property for the light-emitting layer. In addition, the organic semiconductor material described in Embodiment 1 has a bipolar property, and thus can also be used for layers other than the light-emitting layer (e.g., the hole-transport layer and the electron-transport layer). Moreover, the organic semiconductor material described in Embodiment 1 has a large band gap, and thus can also be used for an electron-blocking layer or a hole-blocking layer. Furthermore, the organic semiconductor material described in Embodiment 1 has high triplet excitation energy, and thus can also be used for an exciton-blocking layer.

Any of a variety of methods can be employed for forming the EL layer regardless of whether it is a dry process or a wet process. For example, a vacuum evaporation method, an ink-jet method, a spin coating method or the like may be used. A different formation method may be employed for each electrode or each layer. The organic semiconductor material described in Embodiment 1 exhibits a good sublimation property; thus, a favorable film can be formed by an evaporation method by using the organic semiconductor material. In addition, the organic semiconductor material described in Embodiment 1 also has excellent solubility in a solvent, and thus can be used in deposition by a wet process without any problems.

For example, the EL layer may be formed using a high molecular compound by a wet process. Alternatively, the EL layer can be formed using a low molecular organic compound by a wet process. Further alternatively, the EL layer may be formed using a low molecular organic compound by a dry process such as a vacuum evaporation method.

In addition, the electrode may be formed by a wet method using a sol-gel method, or by a wet method using paste of a metal material. Alternatively, the electrode may be formed by a dry method such as a sputtering method or a vacuum evaporation method.

For example, in the case where a light-emitting element of the present invention is applied to a display device and the display device is manufactured using a large substrate, it is preferable to form the light-emitting layer by a wet method. By forming the light-emitting layer by an ink-jet method, selective deposition of the light-emitting layer for different colors can be easily performed even when a large substrate is used.

In the light-emitting element having the above structure, current flows due to a potential difference generated between the first electrode 102 and the second electrode 104 and holes and electrons are recombined in the EL layer 103, whereby light is emitted.

The emitted light is extracted through one or both of the first electrode 102 and the second electrode 104. Accordingly, one or both of the first electrode 102 and the second electrode 104 is/are an electrode having a light-transmitting property. For example, in the case where only the first electrode 102 has a light-transmitting property, light emission is extracted from the substrate side through the first electrode 102. Meanwhile, in the case where only the second electrode 104 has a light-transmitting property, light emission is extracted from the side opposite to the substrate through the second electrode 104. In the case where each of the first electrode 102 and the second electrode 104 has a light-transmitting property, light emission is extracted from both of the substrate side and the side opposite to the substrate through the first electrode 102 and the second electrode 104.

The structure of the layers provided between the first electrode 102 and the second electrode 104 is not limited to the above structure. Any structure other than the above structure can be employed as long as a light-emitting region for recombination of holes and electrons is positioned away from the first electrode 102 and the second electrode 104 so as to prevent quenching caused by proximity of the light-emitting region to a metal, and the organic semiconductor material described in Embodiment 1 is provided.

In other words, there is no particular limitation on the stacked structure of the layers; layers aimed of a substance having a high electron-transport property, a substance having a high hole-transport property, a substance having a high electron-injection property, a substance having a high hole-injection property, a bipolar substance (a substance having high electron-transport and hole-transport properties), and the like may be combined with the organic semiconductor material described in Embodiment 1 as appropriate to form the stacked structure.

Figure 2:
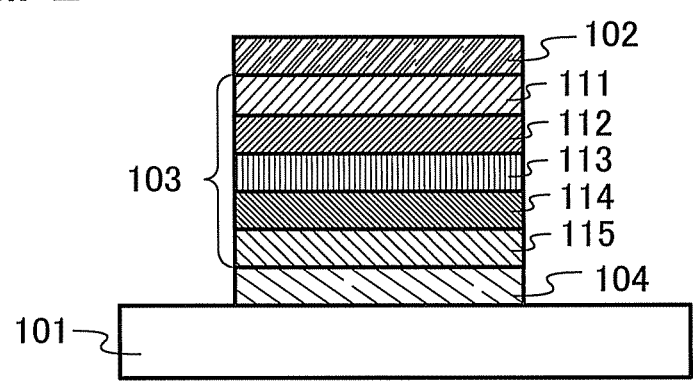
FIG. 2 illustrates a light-emitting element of the present invention.

For example, as illustrated in FIG. 2, a structure may be employed in which the second electrode 104 functioning as a cathode, the EL layer 103, and the first electrode 102 functioning as an anode are stacked in this order over the substrate 101. In FIG. 2, a structure is employed in which the electron-injection layer 115, the electron-transport layer 114, the light-emitting layer 113, the hole-transport layer 112, and the hole-injection layer 111 are stacked in this order over the second electrode 104.

Note that in this embodiment, the light-emitting element is formed over a substrate made of glass, plastic, or the like. By forming a plurality of such light-emitting elements over one substrate, a passive matrix light-emitting device can be manufactured. Alternatively, a transistor may be formed over a substrate made of glass, plastic, or the like, and a light-emitting element may be manufactured over an electrode that is electrically connected to the transistor. In this manner, an active matrix light-emitting device in which the driving of the light-emitting element is controlled by the transistor can be manufactured. Note that the structure of the transistor is not particularly limited. In the case of a thin film transistor (TFT), a staggered TFT or an inverted staggered TFT may be employed. Further, a driver circuit formed in a TFT substrate may include both an n-channel TFT and a p-channel TFT or only one of an n-channel TFT and a p-channel TFT. There is no particular limitation on crystallinity of a semiconductor film used for the TFT. An amorphous semiconductor film may be used, or a crystalline semiconductor film may be used. A single crystal semiconductor film may be used. A single crystal semiconductor film can be formed by Smart Cut (registered trademark) or the like.

Note that this embodiment can be combined with any of the other embodiments as appropriate.

Embodiment 4

In this embodiment, a mode of a light-emitting element in which a plurality of light-emitting units according to the present invention are stacked (hereinafter, such a light-emitting element is also referred to as a stacked-type light-emitting element) will be described with reference to FIG. 3. The light-emitting element is a stacked-type light-emitting element including a plurality of light-emitting units between a first electrode and a second electrode. The structure of each of the light-emitting units can be similar to the structure of the EL layer described in Embodiment 3. In other words, the light-emitting element described in Embodiment 3 is a light-emitting element having one light-emitting unit. In this embodiment, a light-emitting element having a plurality of light-emitting units will be described.

Figure 3:
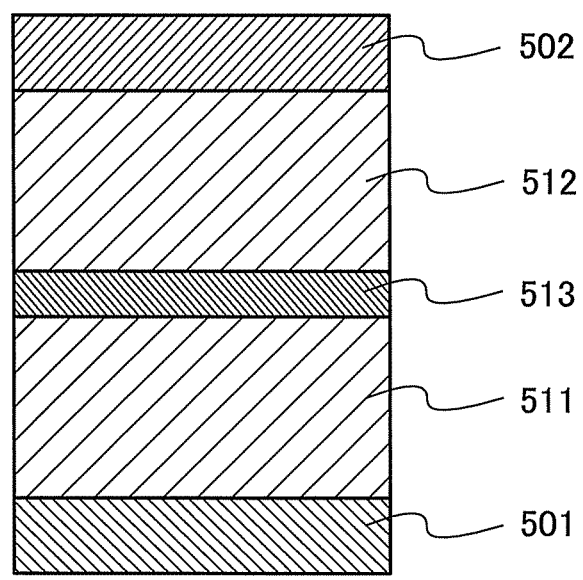
FIG. 3 illustrates a light-emitting element of the present invention.

In FIG. 3, a first light-emitting unit 511 and a second light-emitting unit 512 are stacked between a first electrode 501 and a second electrode 502. A charge generation layer 513 is provided between the first light-emitting unit 511 and the second light-emitting unit 512. Materials similar to those in Embodiment 3 can be applied to the first electrode 501 and the second electrode 502. In addition, the first light-emitting unit 511 and the second light-emitting unit 512 may have the same structure or different structures. Structures of the first light-emitting unit 511 and the second light-emitting unit 512 can be similar to the structure of the EL layer described in Embodiment 3.

The charge generation layer 513 is a layer that injects electrons into one of the light-emitting units and injects holes into the other of the light-emitting unit when a voltage is applied to the first electrode 501 and the second electrode 502. The charge generation layer 513 may have a single-layer structure or a stacked structure. In the case where the charge generation layer 513 has a single-layer structure, any of the electrode materials and the composite materials described in Embodiment 3 can be used. In that case, it is preferable that the light-emitting unit which is positioned closer to an anode than the charge generation layer includes an electron-injection layer. As a stacked structure of plural layers, a structure in which a layer which injects holes and a layer which injects electrons are stacked is preferable.

For the layer which injects holes, a semiconductor or an insulator, such as molybdenum oxide, vanadium oxide, rhenium oxide, or ruthenium oxide, can be used. Alternatively, the hole-injection layer may have a structure in which an acceptor substance is added to a substance having a high hole-transport property. The layer containing a substance having a high hole-transport property and an acceptor substance is formed using the composite material described in Embodiment 3 and includes, as an acceptor substance, 7,7,8,8-tetracyano-2,3,5,6-tetrafluoroquinodimethane ($F_4$-TCNQ) or metal oxide such as vanadium oxide, molybdenum oxide, or tungsten oxide. As the substance having a high hole-transport property, any of a variety of compounds such as aromatic amine compounds, carbazole derivatives, aromatic hydrocarbons, and high molecular compounds (such as oligomers, dendrimers, and polymers) can be used. Note that a substance having a hole mobility of $10^{-6}$ cm$^2$/Vs or higher is preferably used as the substance having a high hole-transport property. Note that any substance other than the above substances may also be used as long as they are substances whose hole-transport property is higher than the electron-transport property. The composite material containing the substance having a high hole-transport property and the acceptor substance has an excellent carrier-injection property and carrier-transport property, and thus makes it possible to realize low-voltage driving and low-current driving.

For the layer which injects electrons, a semiconductor or an insulator, such as molybdenum oxide, vanadium oxide, rhenium oxide, or ruthenium oxide, can be used. Alternatively, the layer which injects electrons may have a structure in which a donor substance is added to a substance having a high electron-transport property. As the donor substance, an alkali metal, an alkaline-earth metal, a rare-earth metal, a metal that belongs to Group 13 of the periodic table, or an oxide or carbonate thereof may be used. Specifically, lithium (Li), cesium (Cs), magnesium (Mg), calcium (Ca), ytterbium (Yb), indium (In), lithium oxide, cesium carbonate, or the like is preferably used. An organic compound such as tetrathianaphthacene may be used as the donor substance. As the substance having a high electron-transport property, any of the materials described in Embodiment 3 can be used. Note that a substance having an electron mobility of $10^{-6}$ cm$^2$/Vs or higher is preferably used as the substance having a high electron-transport property. Note that any substance other than the above substances may also be used as long as they are substances whose electron-transport property is higher than the hole-transport property. The composite material containing the substance having a high electron-transport property and the donor substance has an excellent carrier-injection property and carrier-transport property, and thus makes it possible to realize low-voltage driving and low-current driving.

Alternatively, the charge-generation layer 513 may be formed by combining a layer containing a substance having a high hole-transport property and metal oxide with a transparent conductive film. It is preferable that the charge generation layer have a high light-transmitting property in view of light extraction efficiency.

In any case, the charge-generation layer 513, which is interposed between the first light-emitting unit 511 and the second light-emitting unit 512, is acceptable as long as electrons are injected to one of the light-emitting units and holes are injected to the other of the light-emitting units when voltage is applied to the first electrode 501 and the second electrode 502. For example, in the case of applying voltage so that the potential of the first electrode is higher than that of the second electrode, any structure is acceptable for the charge-generation layer 513 as long as the charge-generation layer 513 injects electrons and holes into the first light-emitting unit 511 and the second light-emitting unit 512, respectively.

Although the light-emitting element having two light-emitting units is described in this embodiment, a light-emitting element in which three or more light-emitting units are stacked can be applied in a similar way. By arranging a plurality of light-emitting units between a pair of electrodes so as to be partitioned by a charge-generation layer as in the light-emitting element of this embodiment, the light-emitting element can perform light emission in a high luminance region while keeping current density low, and thus can have a long lifetime. When the light-emitting element is applied to a lighting device, a drop in voltage due to the resistance of an electrode material can be suppressed; thus, uniform emission in a large area can be achieved. Moreover, a light-emitting device which can be driven at low voltage and has low power consumption can be achieved.

The light-emitting units emit light of different colors from each other, thereby obtaining light emission of desired color as the whole light-emitting element. For example, in a light-emitting element having two light-emitting units, the emission colors of the first light-emitting unit and the second light-emitting unit are made complementary, so that the light-emitting element which emits white light as the whole element can be obtained. Note that "complementary colors" refer to colors that can produce an achromatic color when mixed. In other words, when light of complementary colors is mixed, white light emission can be obtained. The same can be applied to a light-emitting element having three light-emitting units. For example, when the first light-emitting unit emits red light, the second light-emitting unit emits green light and the third light-emitting unit emits blue light, white light can be emitted from the whole light-emitting element.

Note that this embodiment can be combined with any of the other embodiments as appropriate.

Embodiment 5

In this embodiment, a light-emitting device including a light-emitting element of the present invention will be described.

Figure 4A:
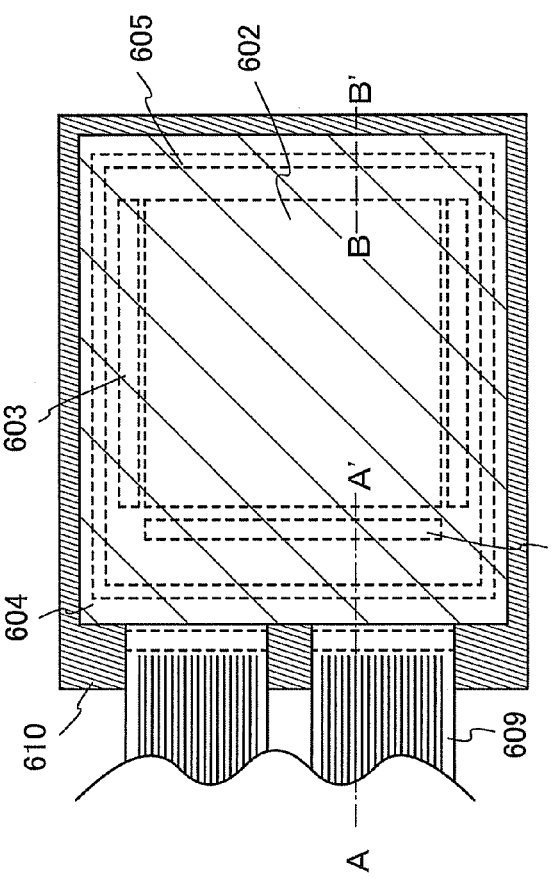
FIGS. 4A and 4B illustrate, a light-emitting device of the present invention.
Figure 4B:
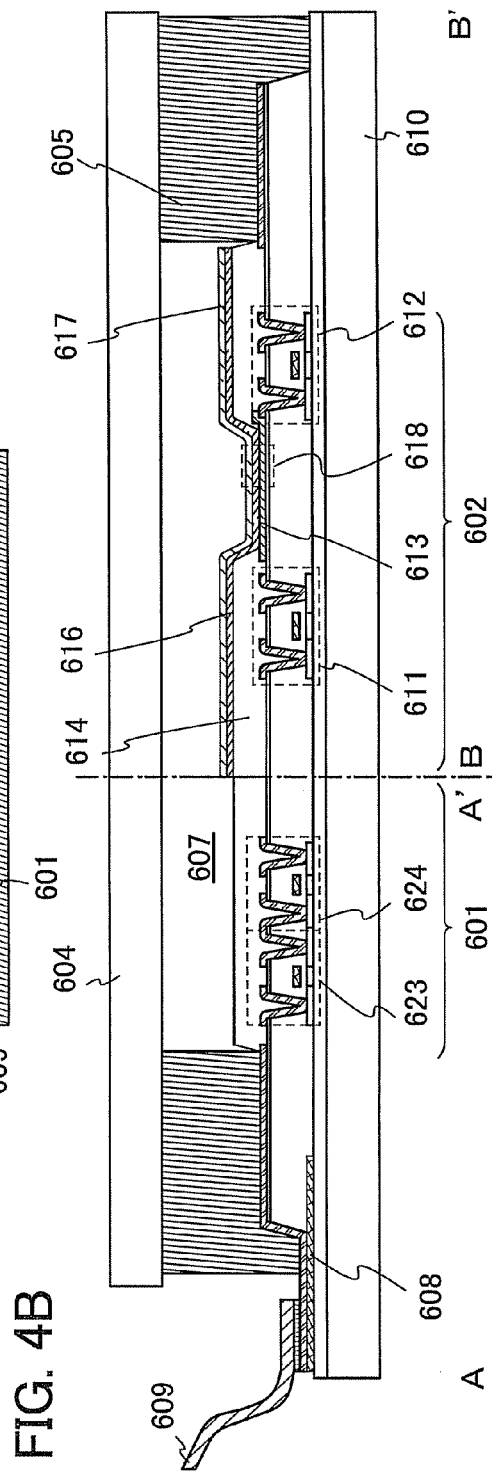

In this embodiment, a light-emitting device having a light-emitting element of the present invention in a pixel portion will be described with reference to FIGS. 4A and 4B. FIG. 4A is a top view illustrating a light-emitting device and FIG. 4B is a cross-sectional view along lines A-A' and B-B' of FIG. 4A. The light-emitting device includes a driver circuit portion (source side driver circuit) 601, a pixel portion 602, and a driver circuit portion (gate side driver circuit) 603, which are indicated by dotted lines, in order to control the light emission from the light-emitting element. Moreover, a reference numeral 604 denotes a sealing substrate; 605, a sealing material; and 607, a space surrounded by the sealant 605.

Reference numeral 608 denotes a wiring for transmitting signals to be inputted into the source side driver circuit 601 and the gate side driver circuit portion 603 and receiving signals such as a video signal, a clock signal, a start signal, and a reset signal from an FPC (flexible printed circuit) 609 serving as an external input terminal. Although only the FPC is illustrated here, a printed wiring board (PWB) may be attached to the FPC. The light-emitting device in this specification includes, in its category, not only the light-emitting device itself but also the light-emitting device provided with the FPC or the PWB.

Next, a cross-sectional structure will be described with reference to FIG. 4B. Although the driving circuit portion and the pixel portion are formed on an element substrate 610, the source side driving circuit 601 that is the driving circuit portion, and one of the pixels in the pixel portion 602 are illustrated here.

Note that as the source side driving circuit 601, a CMOS circuit in which an n-channel TFT 623 and a p-channel TFT 624 are combined is formed. The driver circuit may be formed using various circuits including TFTs, such as a CMOS circuit, a PMOS circuit, or an NMOS circuit. Although a driver-integrated type in which a driver circuit is formed over a substrate provided with a pixel portion is described in this embodiment, the present invention is not limited to this type, and the driver circuit can be formed outside the substrate.

The pixel portion 602 includes a plurality of pixels each having a switching TFT 611, a current controlling TFT 612, and a first electrode 613 that is electrically connected to a drain of the current controlling TFT 612. Note that an insulator 614 is formed to cover the edge portion of the first electrode 613. Here, the insulator 614 is formed using a positive type photosensitive acrylic resin film.

In order to improve the coverage, the insulator 614 is formed to have a curved surface with curvature at its upper or lower end portion. For example, in the case of using positive photosensitive acrylic for the insulator 614, only the upper end portion of the insulator 614 preferably has a curved surface with a radius of curvature of 0.2 μm to 0.3 μm. As the insulator 614, either a negative type which becomes insoluble in etchant by light irradiation or a positive type which becomes soluble in etchant by irradiation with light can be used.

An EL layer 616 and a second electrode 617 are formed over the first electrode 613. Here, the first electrode 613 can be formed using any of a variety of metals, alloys, electrically conductive compounds, and mixtures thereof. In the case where the first electrode is used as an anode, it is preferable to use, among those materials, a metal, an alloy, an electrically conductive compound, a mixture thereof, or the like with a high work function (preferably, a work function of 4.0 eV or higher). For example, the first electrode 613 can be foamed using a single-layer film of an indium tin oxide film containing silicon, an indium zinc oxide film, a titanium nitride film, a chromium film, a tungsten film, a Zn film, a Pt film, or the like; or a stacked film such as a stack of a titanium nitride film and a film containing aluminum as its main component or a three-layer structure of a titanium nitride film, a film containing aluminum as its main component, and a titanium nitride film. Note that when a stacked structure is employed, the first electrode 613 has low resistance as a wiring, forms a favorable ohmic contact, and can serve as an anode.

The EL layer 616 is formed by any of a variety of methods such as an evaporation method using an evaporation mask, an ink-jet method, and a spin coating method. The EL layer 616 contains the organic semiconductor material described in Embodiment 1. Any of low molecular compounds, high molecular compounds, oligomers, and dendrimers may be employed as a material for the EL layer 616. As the material for the EL layer, not only an organic compound but also an inorganic compound may be used.

As the material for the second electrode 617, any of a variety of metals, alloys, electrically conductive compounds, mixtures of these, and the like can be used. In the case where the second electrode is used as a cathode, it is preferable that the second electrode is formed using a metal, an alloy, an electrically conductive compound, a mixture thereof, or the like with a low work function (preferably, a work function of 3.8 eV or lower) among such materials. As an example, an element that belongs to Group 1 or Group 2 of the periodic table, i.e., an alkali metal such as lithium (Li) or cesium (Cs), an alkaline earth metal such as magnesium (Mg), calcium (Ca), or strontium (Sr), or an alloy containing any of these (such as MgAg or AlLi); and the like can be, given. In the case where light generated in the EL layer 616 is transmitted through the second electrode 617, the second electrode 617 can be formed using a stack of a metal thin film and a transparent conductive film (indium tin oxide (ITO), indium tin oxide containing silicon or silicon oxide, indium zinc oxide (IZO), indium oxide containing tungsten oxide and zinc oxide (IWZO), or the like.

Further, a light-emitting element 618 is provided in the space 607 surrounded with the element substrate 610, the sealing substrate 604, and the sealant 605 by pasting the sealing substrate 604 and the element substrate 610 using the sealant 605. Note that the space 607 is filled with a filler such as an inert gas (e.g., nitrogen, argon, or the like) or the sealant 605.

An epoxy-based resin is preferably used for the sealant 605. Such a material is desirably a material that transmits as little moisture or oxygen as possible. As a material for the sealing substrate 604, a plastic substrate made of FRP (Fiber-glass-Reinforced Plastics), PVF (polyvinyl fluoride), polyester, acrylic, or the like can be used besides a glass substrate or a quartz substrate.

In the above manner, the light-emitting device including the light-emitting element of the present invention can be obtained.

The light emitting device of the present invention includes the light emitting element described in Embodiment 3 or 4. The light-emitting element described in Embodiment 3 or Embodiment 4 has high emission efficiency and is driven at low voltage. Thus, a light-emitting device which can emit light with high luminance can be obtained. Further, a light-emitting device with low power consumption can be obtained.

Figure 5A:
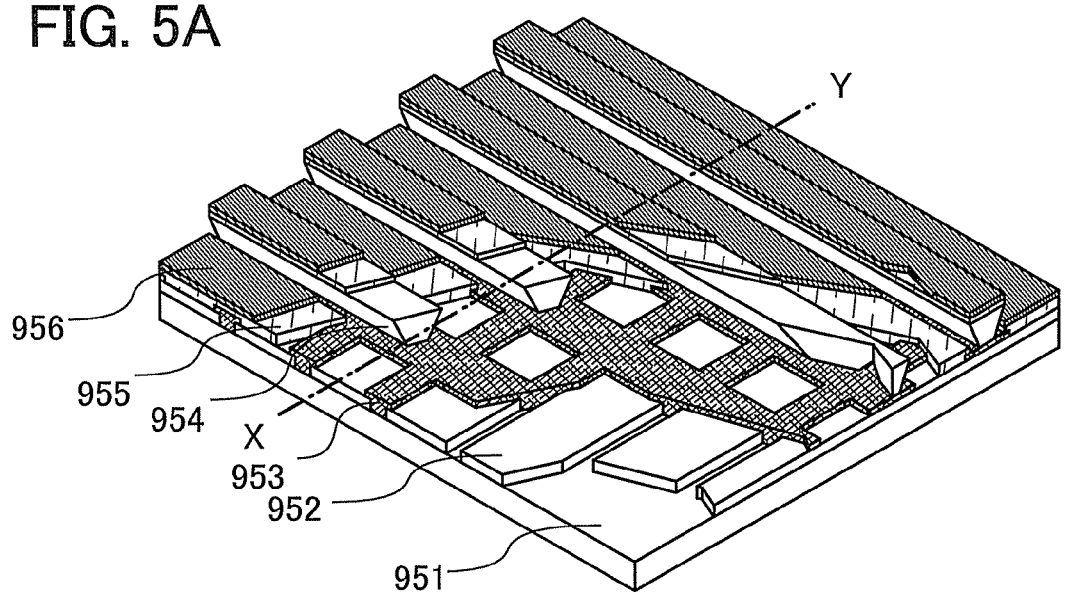
FIGS. 5A and 5B illustrate a light-emitting device of the present invention.
Figure 5B:
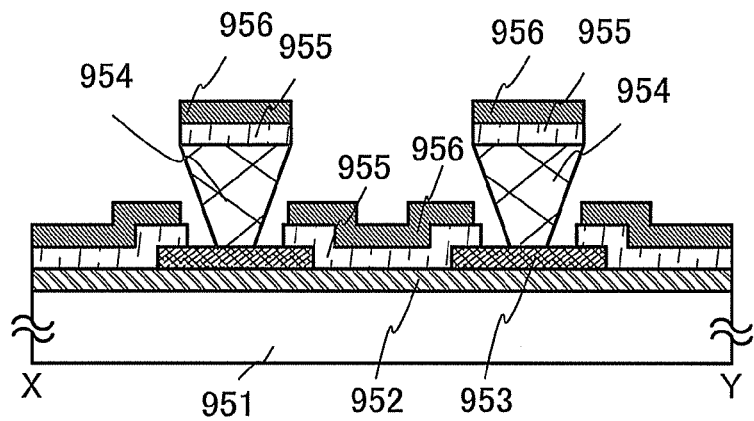

As described above, an active-matrix light-emitting device that controls driving of a light-emitting element with a transistor is described in this embodiment; however, a passive-matrix light-emitting device may be used. FIGS. 5A and 5B illustrate a passive matrix light-emitting device to which the present invention is applied. FIG. 5A is a perspective view of the light-emitting device, and FIG. 5B is a cross-sectional view along a line X-Y of FIG. 5A. In FIGS. 5A and 5B, an EL layer 955 is provided between an electrode 952 and an electrode 956 over a substrate 951. An edge portion of the electrode 952 is covered with an insulating layer 953. A partition layer 954 is provided over the insulating layer 953. The sidewalls of the partition layer 954 are aslope such that the distance between both sidewalls is gradually narrowed toward the surface of the substrate. In other words, a cross section taken along the direction of the short side of the partition wall layer 954 is trapezoidal, and the lower side (a side which is in the same direction as a plane direction of the insulating layer 953 and in contact with the insulating layer 953) is shorter than the upper side (a side which is in the same direction as the plane direction of the insulating layer 953 and not in contact with the insulating layer 953). A cathode can be patterned by providing the partition wall layer 954 in this manner. In addition, in a passive matrix light-emitting device, a light-emitting device with low power consumption can be obtained by including a light-emitting element with high emission efficiency and low driving voltage according to the present invention.

Note that this embodiment can be combined with any of the other embodiments as appropriate.

Embodiment 6

In this embodiment, electronic devices of the present invention, each of which includes the light-emitting device described in Embodiment 4, will be described. The electronic devices of the present invention includes the light-emitting device described in Embodiment 3 or Embodiment 4 and a display portion with low power consumption.

As the electronic device manufactured by using the light-emitting device of the present invention, the following are given: cameras such as video cameras or digital cameras, goggle-type displays, navigation systems, audio reproducing devices (such as car audio components or an audio components), computers, game machines, mobile information terminals (mobile computers, cellular phones, mobile game machines, or electronic books), image reproducing devices equipped with a recording medium (specifically, devices equipped with a display device for reproducing a recording medium such as digital versatile disk (DVD) and displaying the image), and the like. Specific examples of these electronic devices are illustrated n in FIGS. 6A to 6D.

Figure 6A:
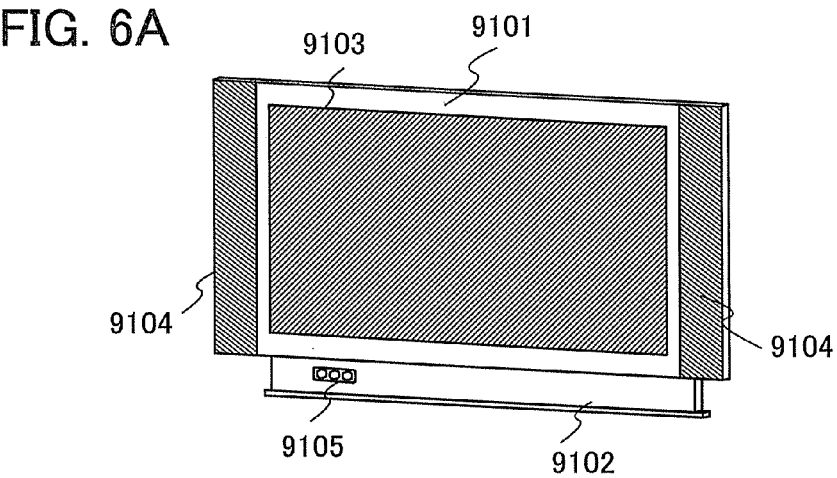
FIGS. 6A to 6D illustrate electronic devices of the present invention.

FIG. 6A illustrates a television device of this embodiment, which includes a housing 9101, a supporting base 9102, a display portion 9103, speaker portions 9104, a video input terminal 9105, and the like. In the display portion 9103 of this television device, light-emitting elements similar to those described in Embodiment 3 or Embodiment 4 are arranged in a matrix. The light-emitting element has features that the emission efficiency is high and the power consumption is low. In addition, the light-emitting element also has a feature that the driving voltage is low. The display portion 9103 which includes the light-emitting element has similar features. Therefore, low power consumption of this television device is achieved. With such features, a power supply circuit can be significantly reduced or downsized in the television device; therefore, reduction in size and weight of the housing 9101 and the supporting base 9102 can be achieved. In the television device of this embodiment, less power consumption and reduction in size and weight are achieved; therefore, the television can be provided as a product which is suitable for the environment.

Figure 6B:
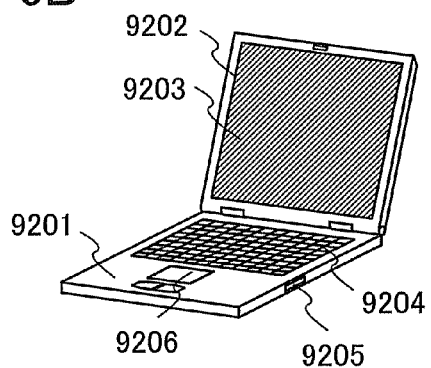

FIG. 6B illustrates a computer of this embodiment, which includes a main body 9201, a housing 9202, a display portion 9203, a keyboard 9204, an external connection port 9205, a pointing device 9206, and the like. In the display portion 9203 of this computer, light-emitting elements similar to those described in Embodiment 3 or Embodiment 4 are arranged in a matrix. The light-emitting element has features that the emission efficiency is high and the power consumption is low. In addition, the light-emitting element also has a feature that the driving voltage is low. The display portion 9203 which includes the light-emitting elements has similar features. Therefore, low power consumption of this computer is achieved. With such features, a power supply circuit can be significantly reduced or downsized in the computer; therefore, reduction in size and weight of the main body 9201 and the housing 9202 can be achieved. In the computer of this embodiment, reduction in power consumption and reduction in size and weight are achieved; therefore, the computer can be provided as a product which is suitable for the environment.

Figure 6C:
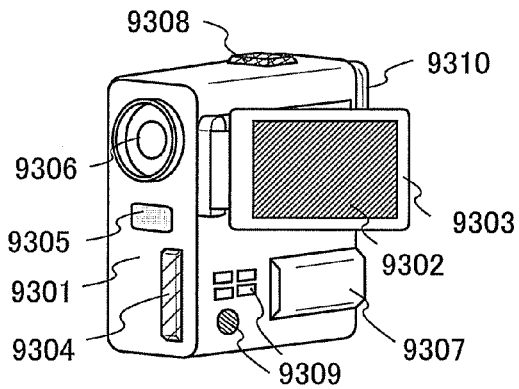

FIG. 6C illustrates a camera of this embodiment, which includes a main body 9301, a display portion 9302, a housing 9303, an external connection port 9304, a remote control receiving portion 9305, an image receiving portion 9306, a battery 9307, an audio input portion 9308, operation keys 9309, an eyepiece portion 9310, and the like. In the display portion 9302 of this camera, light-emitting elements similar to those described in Embodiment 3 or Embodiment 4 are arranged in a matrix. The light-emitting element has features that the emission efficiency is high and the power consumption is low. In addition, the light-emitting element also has a feature that the driving voltage is low. The display portion 9302 which includes the light-emitting elements has similar features. Therefore, low power consumption of this camera is achieved. With such features, a power supply circuit can be significantly reduced or downsized in the camera; therefore, reduction in size and weight of the main body 9301 can be achieved. In the camera of this embodiment, reduction in power consumption and reduction in size and weight are achieved; therefore, the camera can be provided as a product which is suitable for the environment.

Figure 6D:
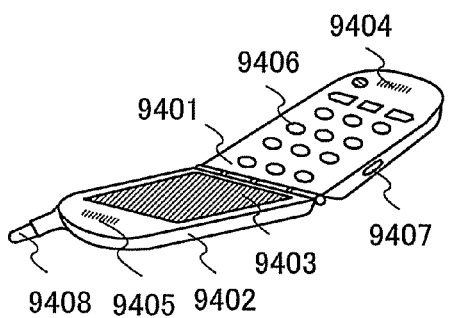

FIG. 6D illustrates a mobile phone of this embodiment, which includes a main body 9401, a housing 9402, a display portion 9403, an audio input portion 9404, an audio output portion 9405, operation keys 9406, an external connection port 9407, an antenna 9408, and the like. In the display portion 9403 of this camera, light-emitting elements similar to those described in Embodiment 3 or Embodiment 4 are arranged in a matrix. The light-emitting element has features that the emission efficiency is high and the power consumption is low. In addition, the light-emitting element also has a feature that the driving voltage is low. The display portion 9403 which includes the light-emitting elements has similar features. Therefore, low power consumption of this camera is achieved. With such features, a power supply circuit can be significantly reduced or downsized in the camera; therefore, reduction in size and weight of the main body 9401 or the housing 9402 can be achieved. In the mobile phone of this embodiment, reduction in power consumption and reduction in size and weight are achieved; therefore, the mobile phone can be provided as a product which is suitable for the environment.

Figure 12A:
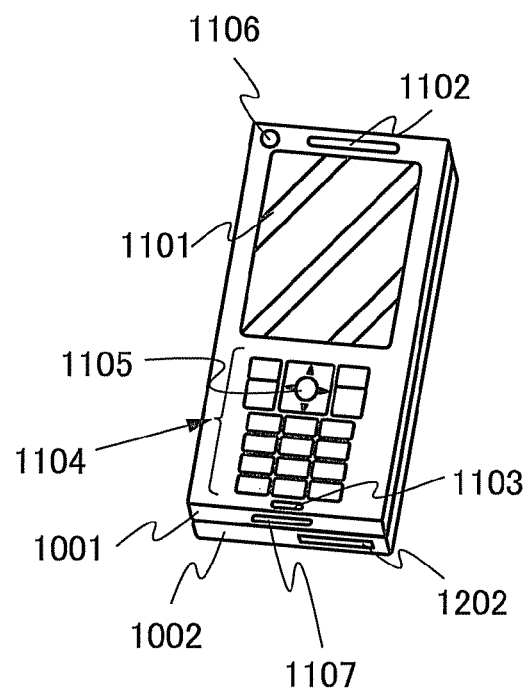
FIGS. 12A to 12C illustrate an electronic device of the present invention.
Figure 12B:
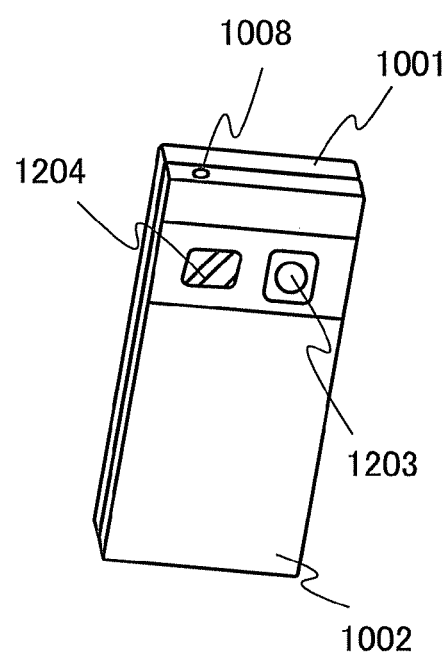
Figure 12C:
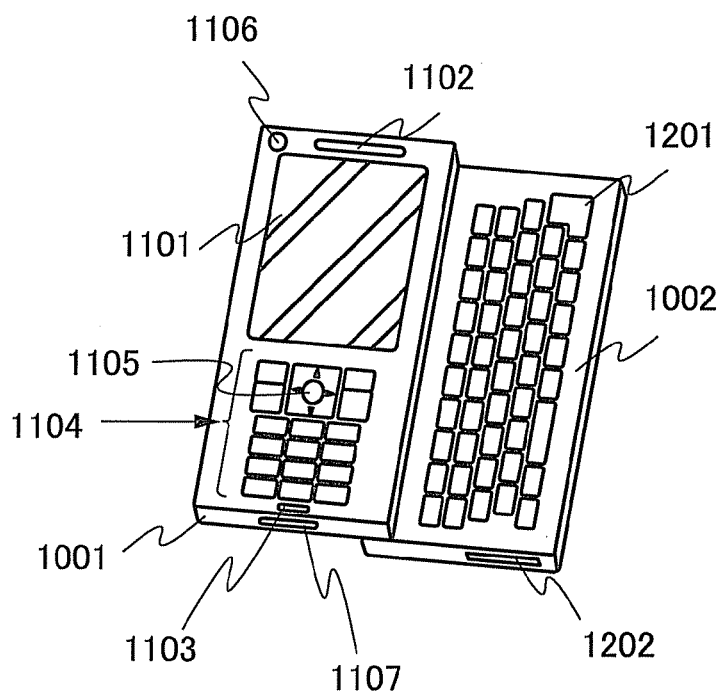

FIGS. 12A to 12C illustrate an example of a structure of a mobile phone, which is different from the structure of the mobile phone of FIG. 6D. FIG. 12A is a front view, FIG. 12B is a rear view, and FIG. 12C is a development view. The mobile phone in FIGS. 12A to 12C is a so-called smartphone which has both a function as a phone and a function as a portable information terminal, and incorporates a computer to conduct a variety of data processing in addition to voice calls.

The mobile phone illustrated in FIGS. 12A to 12C has two housings 1001 and 1002. The housing 1001 includes a display portion 1101, a speaker 1102, a microphone 1103, operation keys 1104, a pointing device 1105, a camera lens 1106, an external connection terminal 1107, an earphone terminal 1108, and the like, while the housing 1002 includes a keyboard 1201, an external memory slot 1202, a camera lens 1203, a light 1204, and the like. In addition, an antenna is incorporated in the housing 1001.

Further, in addition to the above-described structure, the smartphone may incorporate a non-contact IC chip, a small size memory device, or the like.

In the display portion 1101, the light-emitting device described in Embodiment 4 can be incorporated, and a display direction can be changed as appropriate depending on the usage mode. Since the camera lens 1106 is provided in the same plane as the display portion 1101, the smartphone can be used as a videophone. Further, a still image and a moving image can be taken with the camera lens 1203 and the light 1204 by using the display portion 1101 as a viewfinder. The speaker 1102 and the microphone 1103 can be used for video calling, recording and playing sound, and the like without being limited to voice calls. With the use of the operation keys 1104, making and receiving calls, inputting simple information of e-mails or the like, scrolling of the screen, moving the cursor and the like are possible. Furthermore, the housing 1001 and the housing 1002, which are overlapped with each other (FIG. 12A), can be developed by sliding as illustrated in FIG. 12C and can be used as a portable information terminal. At this time, smooth operation can be conducted using the keyboard 1201 and the pointing device 1105. The external connection terminal 1107 can be connected to an AC adaptor and various types of cables such as a USB cable, and charging and data communication with a computer or the like are possible. Furthermore, a large amount of data can be stored and moved by inserting a recording medium into the external memory slot 1202.

In addition to the above-described functions, the mobile phone may have an infrared communication function, a television receiver function, and the like.

Figure 7:
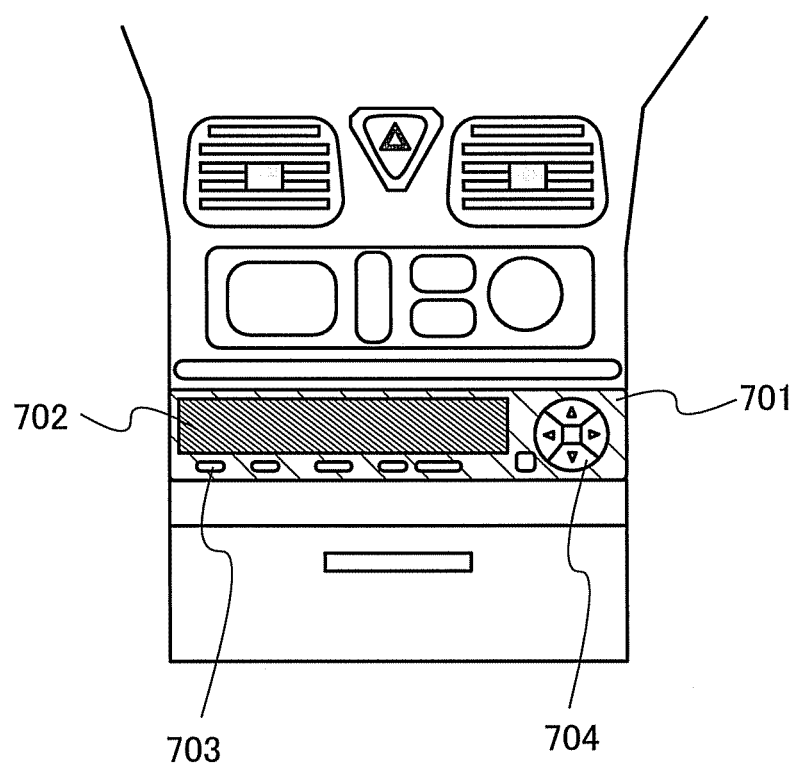
FIG. 7 illustrates an electronic device of the present invention.

FIG. 7 illustrates an audio reproducing device, specifically, a car audio system, which includes a main body 701, a display portion 702, and operation switches 703 and 704. The display portion 702 can be realized using the light-emitting device (passive-matrix type or active-matrix type) described in Embodiment 4. Further, the display portion 702 may employ a segment type light-emitting device. In any case, the use of a light-emitting element of the present invention makes it possible to form a bright display portion while achieving low power consumption, with the use of a vehicle power source (12 V to 42 V). Although an in-car audio system is illustrated in this embodiment, the present invention may be used for a portable audio device or an audio device for household use.

Figure 8:
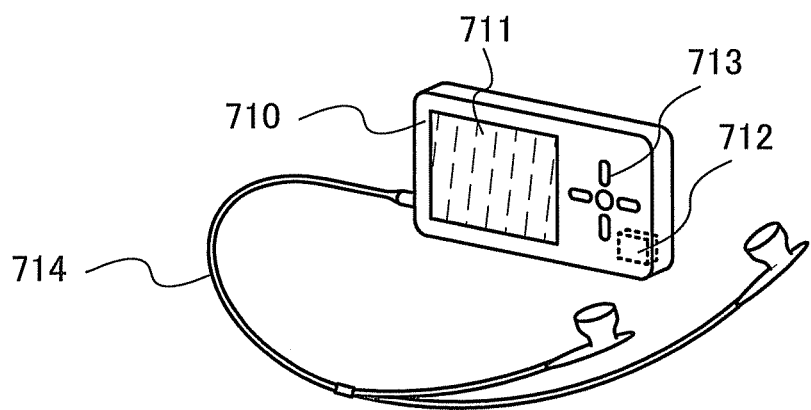
FIG. 8 illustrates an electronic device of the present invention.

FIG. 8 illustrates a digital player as an example of an audio reproducing device. The digital player illustrated in FIG. 8 includes a main body 710, a display portion 711, a memory portion 712, an operation portion 713, earphones 714, and the like. Note that a pair of headphones or a wireless pair of earphones can be used instead of the pair of earphones 714. The display portion 711 can be realized using the light-emitting device (passive-matrix type or active-matrix type) described in Embodiment 6. Further, the display portion 711 may employ a segment type light-emitting device. In any case, the use of a light-emitting element of the present invention makes it possible to form a bright display portion which can display images even when using a secondary battery (a nickel-hydrogen battery or the like) while achieving low power consumption. As the memory portion 712, a hard disk or a nonvolatile memory is used. For example, a NAND type flash memory with a recording capacity of 20 to 200 gigabytes (GB) is used, and by operating the operation portion 713, an image or a sound (e.g., music) can be recorded and reproduced. Note that in the display portion 702 and the display portion 711, white characters are displayed against a black background, and thus, power consumption can be reduced. This is particularly effective for portable audio systems.

As described above, the applicable range of the light-emitting device manufactured by applying the present invention is so wide that the light-emitting device is applicable to electronic devices in various fields. By applying the present invention, an electronic device which has a display portion consuming low power can be manufactured.

The light-emitting device to which the present invention is applied has a light-emitting element with high emission efficiency, and can also be used as a lighting device. A light-emitting device to which the present invention is applied can emit light with high luminance and is preferably used as a lighting device. One mode of using a light-emitting element to which the present invention is applied as a lighting device is described with reference to FIG. 9.

Figure 9:
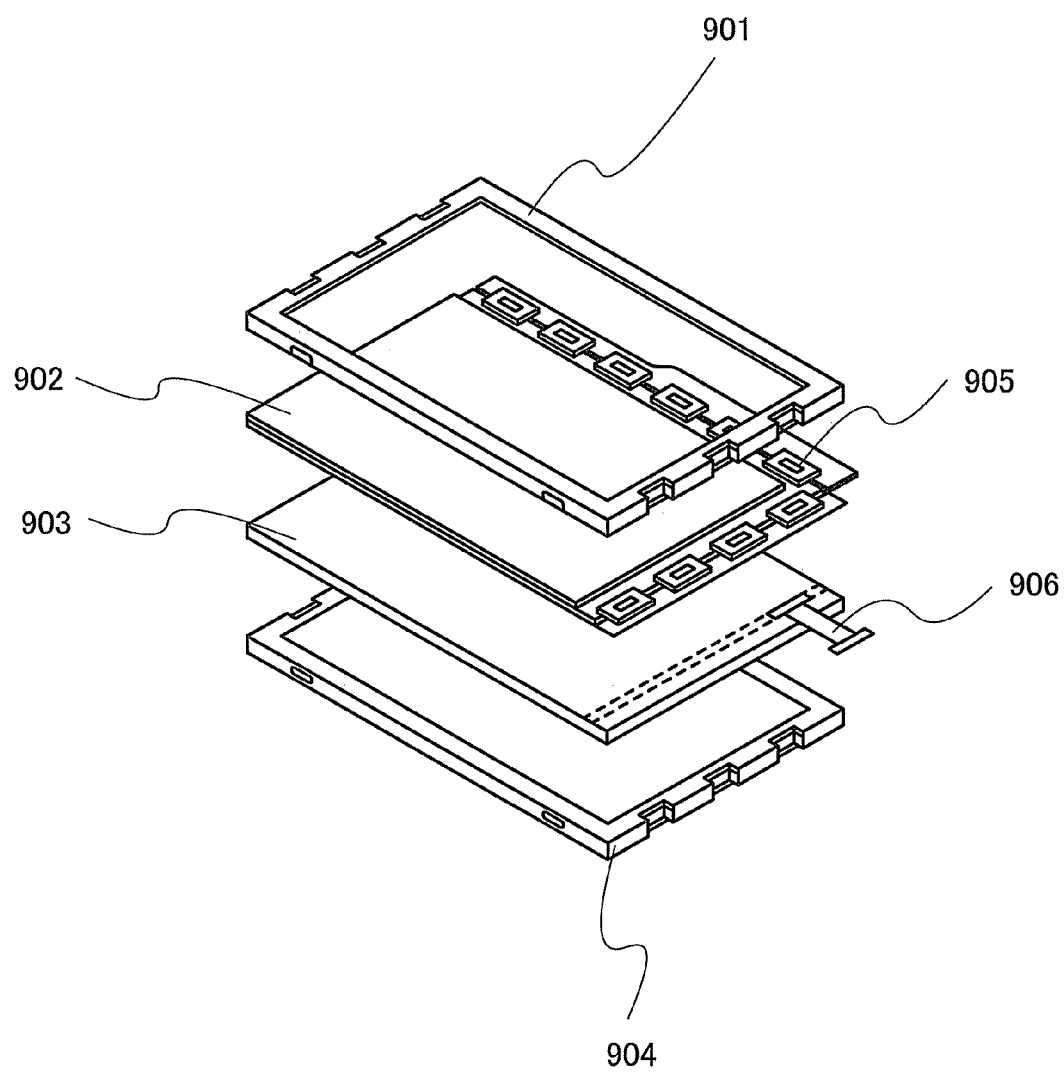
FIG. 9 illustrates an electronic device of the present invention.

FIG. 9 illustrates a liquid crystal display device using the light-emitting device to which the present invention is applied as a backlight, as an example of the electronic device using a light-emitting device according to the present invention as a lighting device. The liquid crystal display device illustrated in FIG. 9 includes a housing 901, a liquid crystal layer 902, a backlight 903, and a housing 904. The liquid crystal layer 902 is connected to a driver IC 905. The light-emitting device to which the present invention is applied is used as the backlight 903, and current is supplied through a terminal 906.

Since the light-emitting device according to the present invention is thin and consumes low power, reduction in thickness and power consumption of a liquid crystal display device is possible by using a light-emitting device according to the present invention as a backlight of the liquid crystal display device. Moreover, a light-emitting device according to the present invention is a plane-emission lighting device and can have a large area. Thus, the backlight can have a large area, and a liquid crystal display device having a large area can also be obtained.

Figure 10:
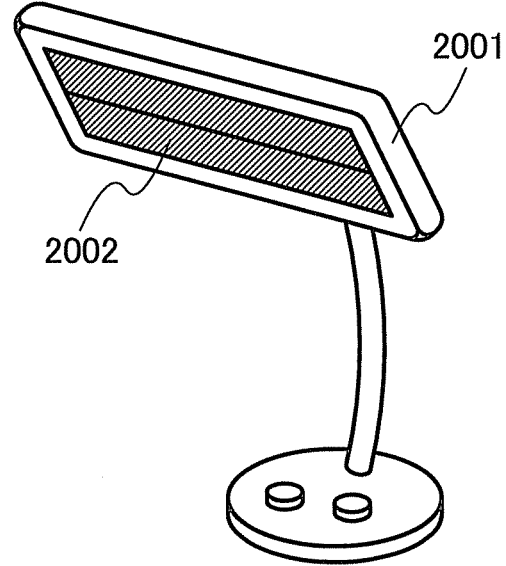
FIG. 10 illustrates a lighting device of the present invention.

FIG. 10 illustrates an example in which a light-emitting device according to the present invention is used for a desk lamp, which is one of lighting devices. The desk lamp illustrated in FIG. 10 includes a housing 2001 and a light source 2002, and a light-emitting device according to the present invention is used as the light source 2002. Since a light-emitting device of the present invention consumes low power, the desk lamp also consumes low power.

Figure 11:
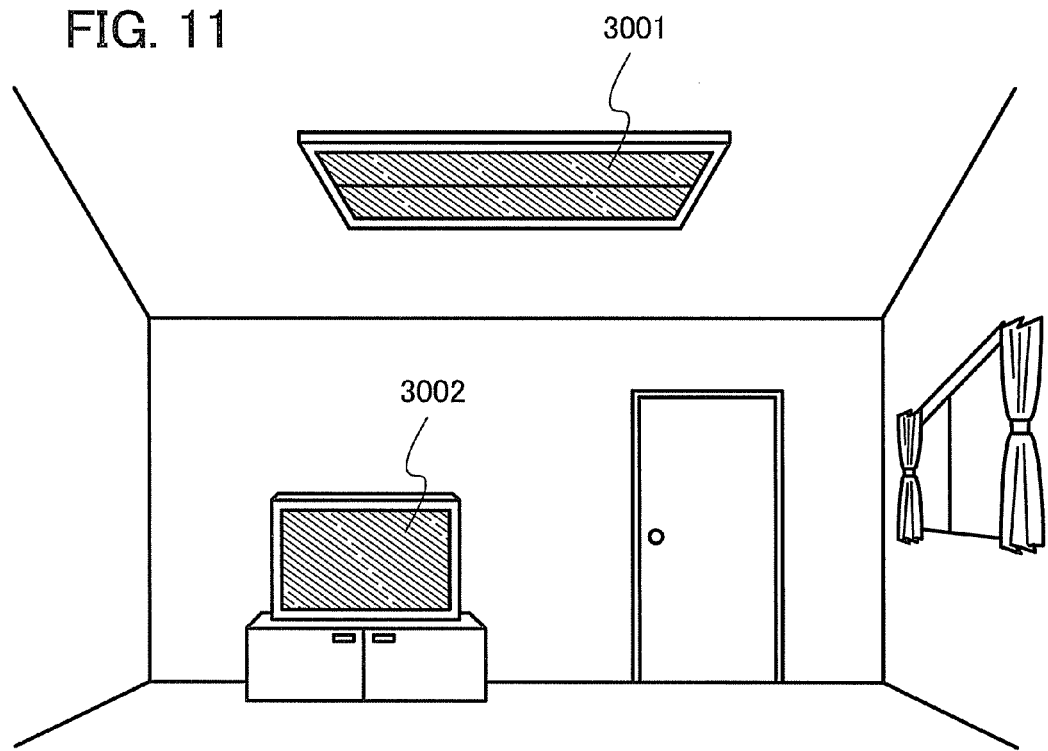
FIG. 11 illustrates a lighting device of the present invention.

FIG. 11 illustrates an example in which the light-emitting device to which the present invention is applied is used for an indoor lighting device 3001. Since a light-emitting device according to the present invention can have a large area, it can be used for a lighting device having a large area. Moreover, because a light-emitting device according to the present invention consumes low power, it can be used for a lighting device which consumes low power. A television device 3002 according to the present invention as illustrated in FIG. 6A is placed in a room where the light-emitting device to which the present invention is applied is used as the indoor lighting device 3001. Thus, public broadcasting and movies can be watched. In such a case, since both devices consume low power, environmental load can be reduced.

Note that this embodiment can be combined with any of the other embodiments as appropriate.

Example 1

Synthesis Example 1

In this synthesis example, a synthesis method of 4-phenyl-4'-{9-[4-(1-phenyl-1H-benzimidazol-2-yl)-phenyl]-fluoren-9-yl}-triphenylamine (abbreviation: F-BPA-Pbim) that is one of the organic semiconductor materials represented by General Formula (G1) described in Embodiment 1 will be specifically described. A structural formula of F-BPA-Pbim is shown below.

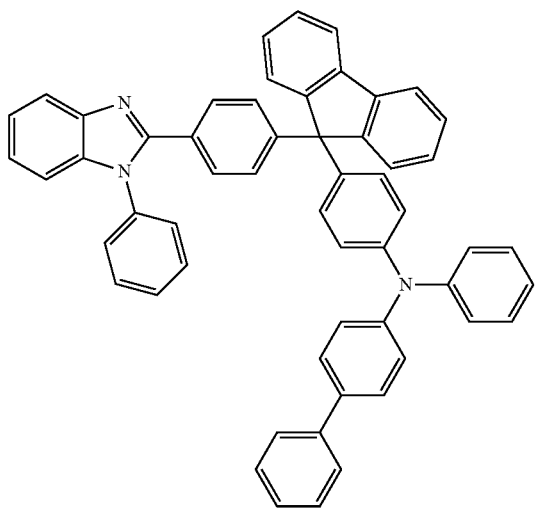

Step 1: Synthesis of 4-bromophenyl-4-(1-phenyl-1H-benzimidazol-2-yl)-phenyl-methanone In a 300 mL three-neck flask, 410 mg (17 mmol) of active magnesium was stirred in 5 mL of dehydrated tetrahydrofuran (THF), and about 0.2 mL of 1,2-dibromoethane was added thereto, so that bubble release and heat generation were confirmed. A solution in which 5.2 g (15 mmol) of 4-bromophenyl-1-phenyl-1H-benzimidazole has been dissolved in 50 mL of dehydrated THF was added thereto. The mixture was heated and stirred for 4 hours, and then cooled to room temperature, so that a Grignard reagent was prepared. Then, in a 500 mL three-neck flask were put 3.7 g (17 mmol) of 4-bromobenzoyl chloride and 150 mL of dehydrated THF, and the mixture was stirred at −40° C. The above Grignard reagent was dropped into the mixture, the mixture was stirred for 1 hour, and then stirred at room temperature for about 15 hours. After reaction, 1N-hydrochloric acid was added to the mixture until the mixed solution became acid. An organic phase of the obtained mixed solution was washed with water, and then magnesium sulfate was added thereto so that moisture was adsorbed. This suspension was filtered, the resulting filtrate was concentrated, and ethyl acetate and toluene were added to perform recrystallization. As a result, 2.5 g of powder was obtained. The reaction scheme is shown in (A-1).

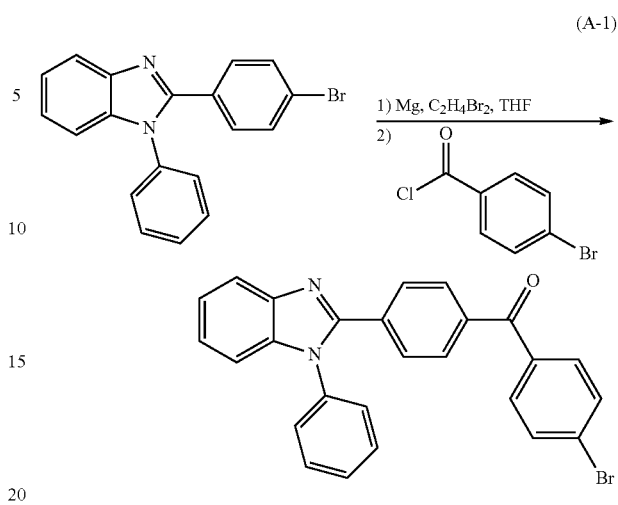

The molecular weight of the obtained compound was measured with a GC/MS detector (ITQ1100 ion trap GC/MS system, manufactured by Thermo Fisher Scientific Inc.). According to the measurement, it was confirmed that a main peak with a molecular weight of 453.28 (mode was EI+) was detected and 4-bromophenyl-4-(1-phenyl-1H-benzimidazol-2-yl)-phenyl-methanone that was an objective substance of the synthesis was obtained.

Step 2: Synthesis of 2-{4-[9-(4-bromophenyl)-fluoren-9-yl]-phenyl}-1-phenyl-1H-benzimidazole In a 200 mL three-neck flask, 1.4 g (6.0 mmol) of 2-bromophenyl which had been dissolved in 20 mL of dehydrated THF was stirred at −80° C. A suspension in which 2.5 g of 4-bromophenyl-4-(1-phenyl-1H-benzimidazol-2-yl)-phenyl-methanone had been mixed with 50 mL of dehydrated THF was dropped to the solution and the mixture was stirred for about 15 hours, whereby an alcohol was formed. After reaction, 1N-hydrochloric acid was added to the mixture until the mixed solution became acid. An organic phase of the obtained mixed solution was washed with water, and then was concentrated. The obtained concentrate was mixed with 30 mL of glacial acetic acid and 1 mL of concentrated hydrochloric acid, and the mixture was heated and stirred at 135° C. for 8 hours. After reaction, this reaction solution was added to water and the obtained solid was washed with water. Hexane was added and the mixture was washed with ultrasonic waves. As a result, 100 mg of white powder was obtained. The reaction scheme is shown in (A-2).

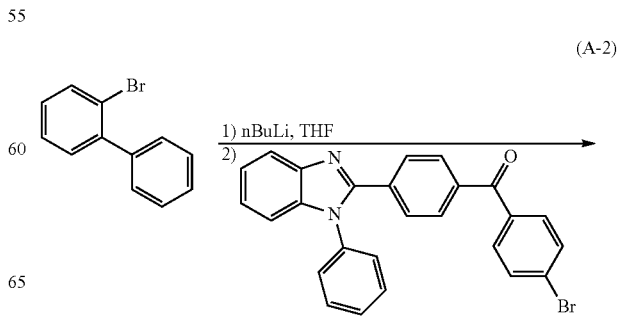

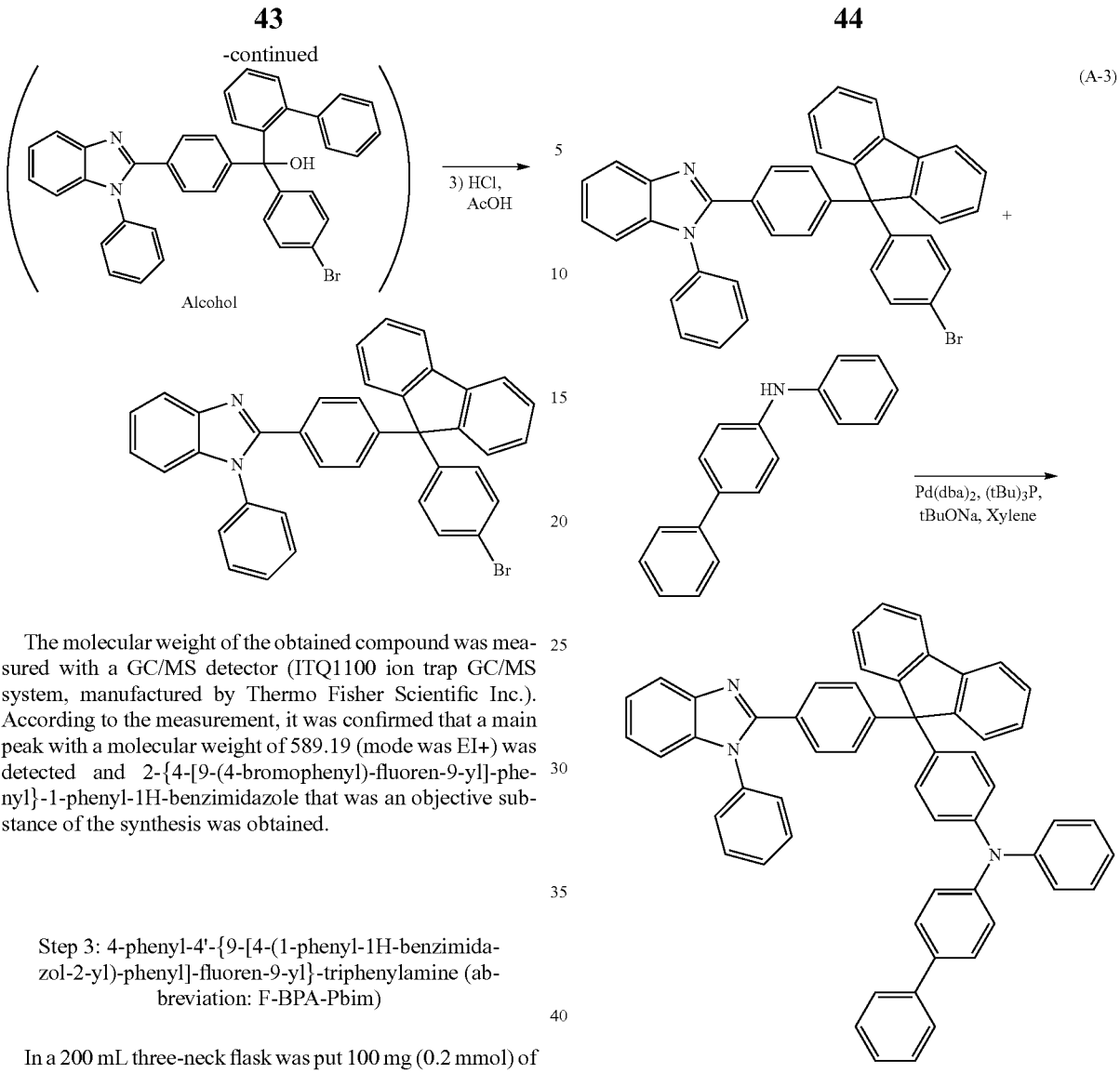

The molecular weight of the obtained compound was measured with a GC/MS detector (ITQ1100 ion trap GC/MS system, manufactured by Thermo Fisher Scientific Inc.). According to the measurement, it was confirmed that a main peak with a molecular weight of 589.19 (mode was EI+) was detected and 2-{4-[9-(4-bromophenyl)-fluoren-9-yl]-phenyl}-1-phenyl-1H-benzimidazole that was an objective substance of the synthesis was obtained.

Step 3: 4-phenyl-4'-{9-[4-(1-phenyl-1H-benzimidazol-2-yl)-phenyl]-fluoren-9-yl}-triphenylamine (abbreviation: F-BPA-Pbim)

In a 200 mL three-neck flask was put 100 mg (0.2 mmol) of 2-{4-[9-(4-bromophenyl)-fluoren-9-yl]-phenyl}-1-phenyl-1H-benzimidazole, 50 mg (0.2 mmol) of 4-biphenylphenylamine, 500 mg (0.5 mmol) of sodium tert-butoxide, and 5.0 mg (10 μmol) of bis(dibenzylideneacetone)palladium(0), and the atmosphere in the flask was substituted with nitrogen. In the mixture was put 10 mL of dehydrated xylene. After the mixture was degassed by being stirred under reduced pressure, 60 μL (30 μmol) of tri(tert-butyl)phosphine (a 10 wt % hexane solution) was added. This mixture was heated and stirred under a nitrogen atmosphere at 130° C. for 2.5 hours to be reacted.

After the reaction, 50 mL of toluene was added to the reaction mixed solution, and the resulting suspension was filtrated through Florisil (Catalog No. 540-00135, produced by Wako Pure Chemical Industries, Ltd.). The obtained filtrate was washed with water, and magnesium sulfate was added thereto so that moisture was adsorbed. This suspension was filtered to obtain a filtrate. The obtained filtrate was concentrated and purified by silica gel column chromatography (developing solvent, toluene: ethyl acetate=10:1). The obtained fraction was concentrated, and acetone and methanol were added. The mixture was irradiated with ultrasonic waves and then recrystallized. As a result, 20 g of powder was obtained. The reaction scheme is shown in (A-3) below.

The Rf values of the obtained powder, 2-{4-[9-(4-bromophenyl)-fluoren-9-yl]-phenyl}-1-phenyl-1H-benzimidazole, and 4-biphenylphenylamine were respectively 0.45, 0.39, and 0.64, which were obtained by silica gel thin layer chromatography (TLC) (with the ratio of developing solvent of ethyl acetate to hexane of 1:2).

The compound which was obtained through Step 3 described above was measured by a nuclear magnetic resonance (NMR) method. The measurement data are shown below. The measurement data show that F-BPA-Pbim (abbreviation) which was an objective substance of the synthesis was obtained.

$^1$H NMR (CDCl$_3$, 300 MHz): δ (ppm)=6.92 (d, J=8.7 Hz, 2H), 6.99-7.56 (m, 28H), 7.75 (d, J=7.2 Hz, 2H), 7.84 (d, J=7.8 Hz, 1H).

Figure 13A:
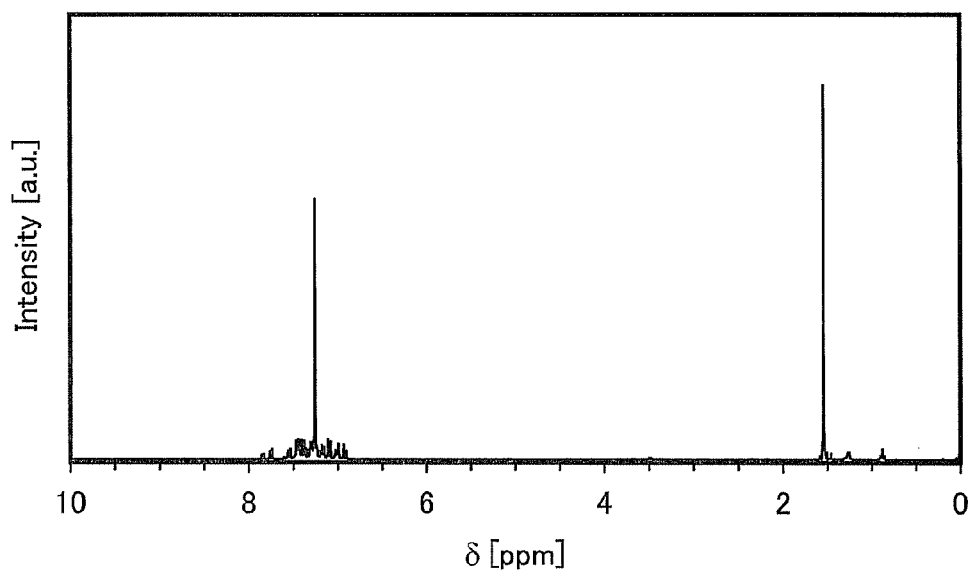
FIGS. 13A and 13B are NMR charts of F-BPA-Pbim.
Figure 13B:
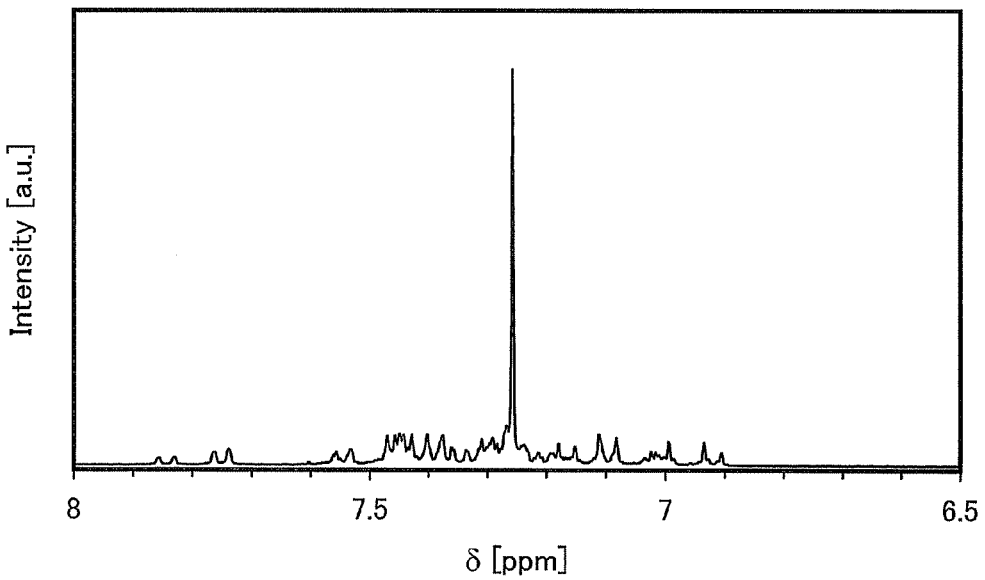

FIGS. 13A and 13B are $^1$H NMR charts. Note that FIG. 13B is an enlarged chart of FIG. 13A. The measurement results confirmed that F-BPA-Pbim (abbreviation) which was an objective substance of the synthesis was obtained.

Further, the molecular weight of the obtained compound was measured with a GC/MS detector (ITQ1100 ion trap GC/MS system, manufactured by Thermo Fisher Scientific Inc.). According to the measurement, it was confirmed that a main peak with a molecular weight of 753.3 (mode was EI+)

was detected and F-BPA-Pbim (abbreviation) that was an objective substance of the synthesis was obtained.

Figure 14:
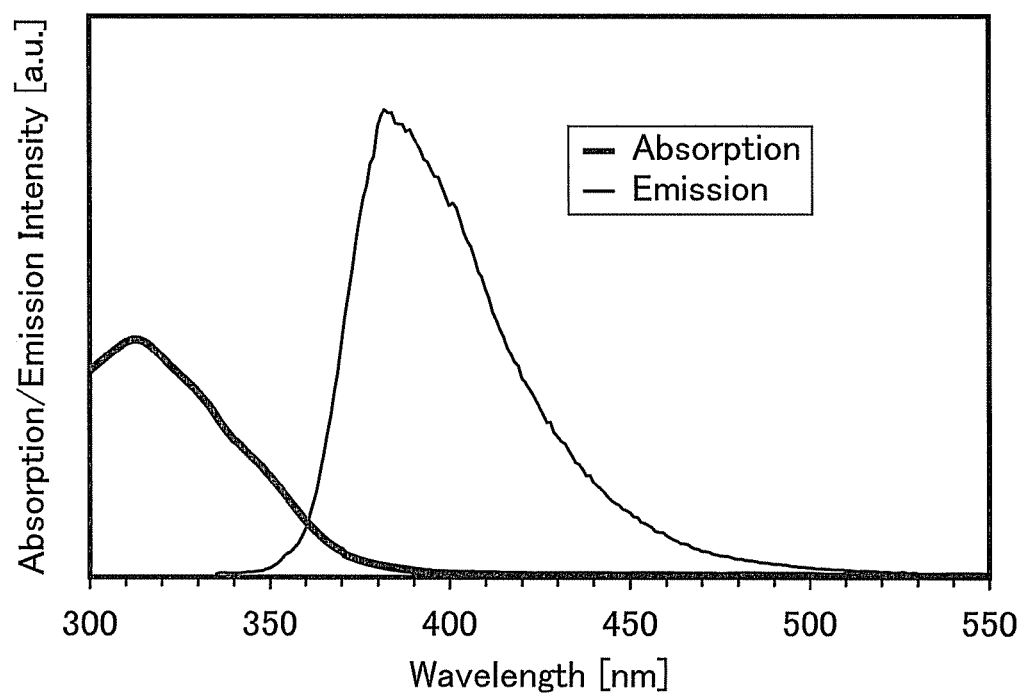
FIG. 14 is a graph showing the absorption spectrum and the emission spectrum of F-BPA-Pbim.

FIG. 14 shows the absorption spectrum and the emission spectrum of F-BPA-Pbim in toluene solution of F-BPA-Pbim. The absorption spectrum was measured with an ultraviolet-visible spectrophotometer (V-550, manufactured by JASCO Corporation). The absorption spectrum shown in FIG. 14 was obtained in such a manner that the absorption spectrum of the toluene solution of F-BPA-Pbim in a quartz cell was measured, and then the absorption spectrum of toluene in the quartz cell was subtracted from the absorption spectrum of the toluene solution of F-BPA-Pbim in the quartz cell. The emission spectrum was measured with the ultraviolet-visible spectrophotometer (V-550, manufactured by JASCO Corporation) which is the same as that for the measurement of the absorption spectrum. F-BPA-Pbim and toluene were put in a quartz cell to measure the emission spectrum of F-BPA-Pbim. According to the measurement of the absorption spectrum and the emission spectrum, the absorption peak wavelength of F-BPA-Pbim in the toluene solution was around 310 nm and the emission peak wavelength thereof was around 384 nm (excitation wavelength: 320 nm).

Example 2

In this example, the most stable structure of a fluorene compound, 4-phenyl-4'-{9-[4-(1-phenyl-1H-benzimidazol-2-yl)-phenyl]-fluoren-9-yl}-triphenylamine (abbreviation: F-BPA-Pbim) that is an organic semiconductor material of one embodiment of the present invention and is represented by General Formula (G1) in Embodiment 1, in the singlet state was calculated using a density functional theory. As a basis function, 6-311 (a basis function of a triple-split valence basis set using three contraction functions for each valence orbital) was applied to all the atoms. By the above basis function, for example, orbits of 1s to 3s are considered in the case of hydrogen atoms while orbits of 1s to 4s and 2p to 4p are considered in the case of carbon atoms. Furthermore, for improvement of the calculation accuracy, the p function and the d function as polarization basis sets were added respectively to hydrogen atoms and atoms other than hydrogen atoms. As a functional, B3LYP was used. In addition, the lowest unoccupied molecular orbital (abbreviation: LUMO) and the highest occupied molecular orbital (abbreviation: HOMO) of the structure were calculated.

Note that Gaussian 09 was used as a quantum chemistry computational program. A high performance computer (Altix 4700 manufactured by SGI Japan, Ltd.) was used for the calculations.

Figure 15A:
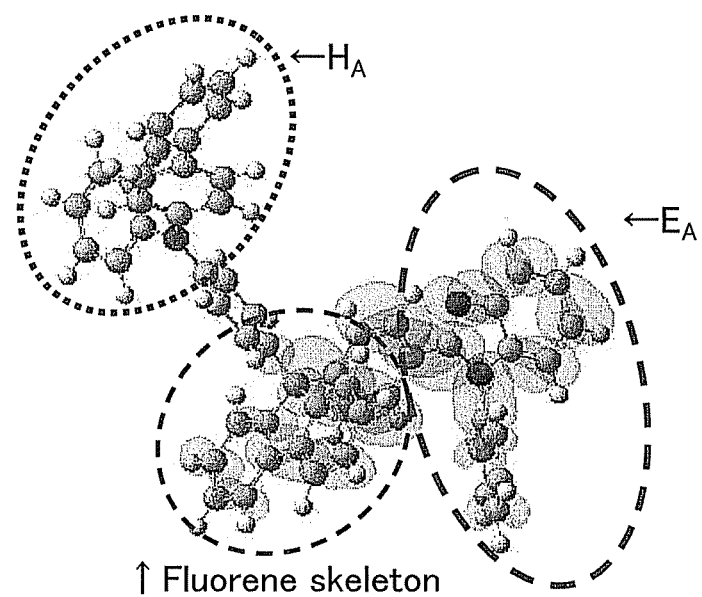
FIGS. 15A and 15B are views showing the HOMO and the LUMO of F-BPA-Pbim.
Figure 15B:
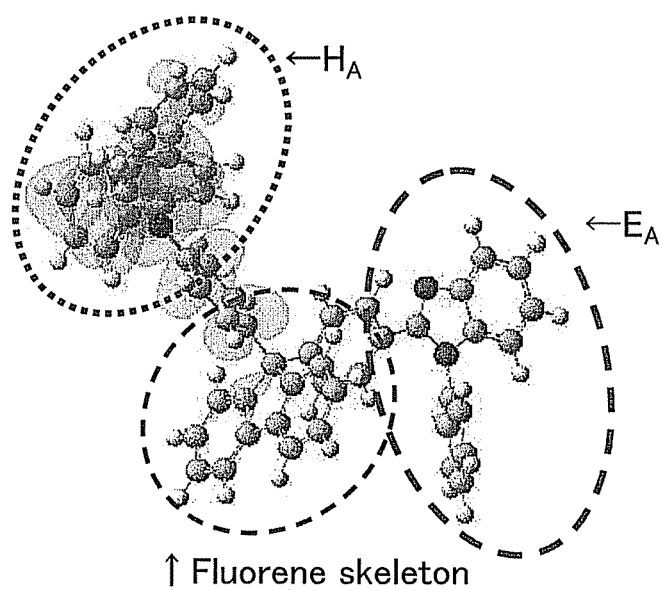

FIGS. 15A and 15B respectively show the LUMO of F-BPA-Pbim and the HOMO thereof.

FIG. 15A shows that the LUMO is spread over a benzimidazole skeleton which is an electron-accepting unit ($E_A$) and a fluorene skeleton and is not spread over a hole-accepting unit ($H_A$). FIG. 15B shows that the HOMO is spread over an amine skeleton which is the hole-accepting unit ($H_A$) and part of the fluorene skeleton and is not spread over the electron-accepting unit $E_A$.

The above calculations indicated that the spread of the HOMO and the spread of the LUMO hardly overlap in F-BPA-Pbim in which the hole-accepting unit and the electron-accepting unit are bonded through sigma bonds of carbon at the 9-position of fluorene. This indicated that F-BPA-Pbim has a large band gap and a high T1 level (the lowest triplet excitation energy level) while having the hole-accepting unit and the electron-accepting unit in the same molecule.

Next, the most stable structure in the triplet state was calculated. The energy of the T1 level was calculated from an energy difference between the most stable structures in the singlet state and in the triplet state. The quantum chemistry computational program used here is Gaussian 09. As a basis function, 6-311G (d, p) was used. As a functional, B3LYP was used.

According to the calculation result, the T1 level of F-BPA-Pbim was 2.64 eV.

The above result also indicated that F-BPA-Pbim has a high T1 level. In addition, the reason for the above was indicated as follows: the hole-accepting unit ($H_A$) and the electron-accepting unit ($E_A$) are bonded through sigma bonds of carbon at the 9-position of fluorene in F-BPA-Pbim, which hinders extension of it conjugation.

Next, the most stable structure of a compound (BPABIm) represented by Chemical Formula (i) below in the singlet state was calculated. This compound has a structure in which the electron-accepting unit ($E_A$) and the hole-accepting unit ($H_A$) of the fluorene compound (F-BPA-Pbim) that is one embodiment of the present invention are bonded without sigma bonds of carbon at the 9-position of fluorene interposed therebetween (that is, a structure in which fluorene skeleton is not included).

[Chemical Formula 34]

The quantum chemistry computational program used here is Gaussian 09. As a basis function, 6-311G (d, p) was adopted. As a functional, B3LYP was used. In addition, the lowest unoccupied molecular orbital (abbreviation: LUMO) and the highest occupied molecular orbital (abbreviation: HOMO) of the structure were calculated.

Figure 16A:
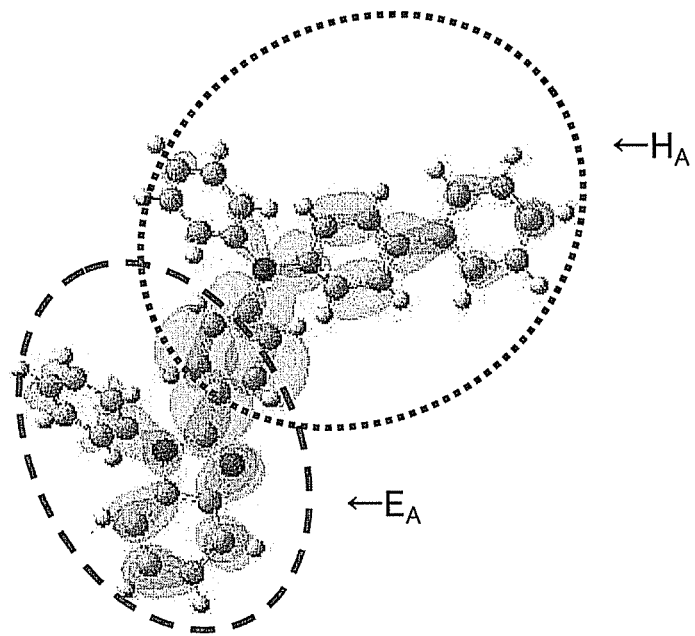
FIGS. 16A and 16B are views showing the HOMO and the LUMO of BPABIm.
Figure 16B:
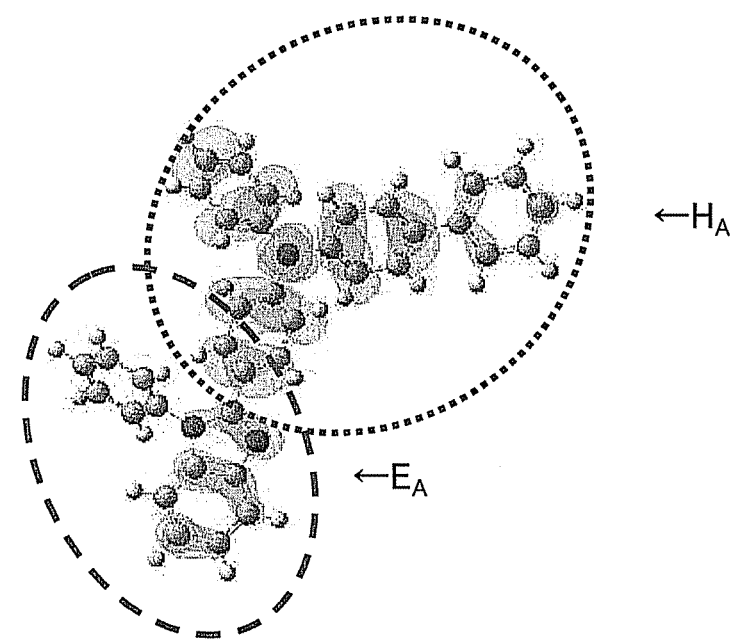

FIGS. 16A and 16B respectively show the LUMO of BPA-BIm and the HOMO thereof. FIG. 16A shows that the LUMO is spread over from a benzimidazole skeleton which is an electron-accepting unit ($E_A$) to part of an amine skeleton which is a hole-accepting unit ($H_A$). FIG. 16B shows that the HOMO is spread over from the amine skeleton which is the hole-accepting unit ($H_A$) to part of the benzimidazole skeleton which is the electron-accepting unit ($E_A$).

Next, the energy of the T1 level was calculated using the molecular structure which was structurally optimized. The quantum chemistry computational program used here is Gaussian 09. As a basis function, 6-311G (d, p) was used. As a functional, B3LYP was used.

According to the calculations, the T1 level of the compound (BPABIm) represented by Chemical Formula (i) was 2.47 eV.

According to the above calculation, F-BPA-Pbim that is one of the organic semiconductor materials and is represented by General Formula (G1) in Embodiment 1 has little overlap of spread of the HOMO and the LUMO as compared to BPABIm. That is, it was indicated that F-BPA-Pbim that is one of the organic semiconductor materials and is represented by General Formula (G1) in Embodiment 1 has a high T1 level even if F-BPA-Pbim has a large molecular amount because the hole-accepting unit ($H_A$) and the electron-accepting unit ($E_A$) are bonded through sigma bonds of carbon at the 9-position of fluorene.

The above results indicated that F-BPA-Pbim that is one of the organic semiconductor materials and is represented by General Formula (G1) in Embodiment 1 has a high T1 level because the hole-accepting unit ($H_A$) and the electron-accepting unit ($E_A$) are bonded through sigma bonds of carbon at the 9-position of fluorene skeleton.

Figure 17:
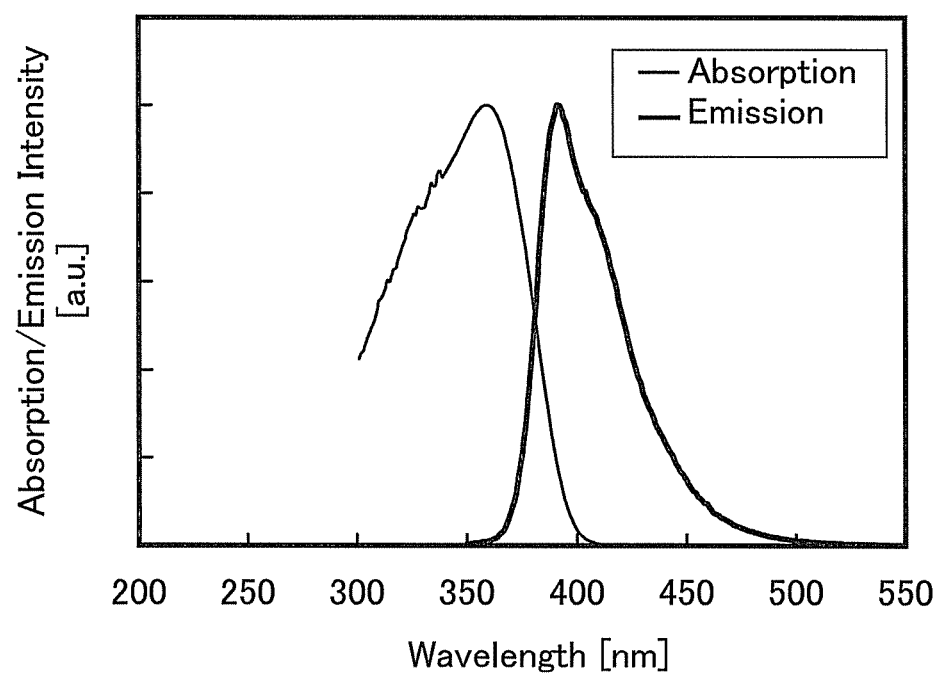
FIG. 17 is a graph showing the absorption spectrum and the emission spectrum of BPABIm.

FIG. 17 shows the absorption spectrum and the emission spectrum of BPABIm in toluene solution.

It was found that the wavelengths of both the absorption spectrum and the emission spectrum of F-BPA-Pbim that is one of the organic semiconductor materials and is represented by General Formula (G1) in Embodiment 1 were shorter than those of the absorption spectrum and the emission spectrum of BPABIm.

Thus, it was indicated that F-BPA-Pbim that is one of the organic semiconductor materials and is represented by General Formula (G1) in Embodiment 1 has a high a S1 level and a large band gap (Bg) between the HOMO level and the LUMO level even if F-BPA-Pbim has a large molecular amount because the hole-accepting unit ($H_A$) and the electron-accepting unit ($E_A$) are bonded through sigma bonds of carbon at the 9-position of fluorene.

Therefore, it was found that the organic semiconductor material that is one embodiment of the present invention can be favorably used for a light-emitting element which emits light with a shorter wavelength.

This application is based on Japanese Patent Application serial no. 2010-190712 filed with the Japan Patent Office on Aug. 27, 2010, the entire contents of which are hereby incorporated by reference.

What is claimed is:

1. An organic compound represented by General Formula (G1):

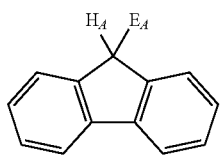

(G1)

wherein $E_A$ is an 1,3-azole group or a phenyl group substituted with an 1,3-azole group, and
wherein $H_A$ represents a hole-accepting unit.

2. The organic compound according to claim 1, wherein the $E_A$ is a phenyl group substituted with an 1,3-azole group.

3. The organic compound according to claim 1, wherein the $H_A$ is a phenyl group having a π-electron rich heteroaromatic substituent or a phenyl group substituted with a diarylamino group.

4. The organic compound according to claim 1, wherein the organic compound is an organic semiconductor material.

5. A light-emitting element comprising the organic compound according to claim 1 between a pair of electrodes.

6. A light-emitting element comprising:
a light-emitting layer comprising the organic compound according to claim 1 and a phosphorescent compound, between a pair of electrodes.

7. A light-emitting element comprising:
a layer comprising the organic compound according to claim 1, between a pair of electrodes; and
a light-emitting layer comprising a phosphorescent compound, between the layer and one of the pair of electrodes.

8. A light-emitting element comprising a light-emitting layer comprising the organic compound according to claim 1.

9. A light-emitting device comprising:
a light-emitting element comprising the organic compound according to claim 1; and
a control circuit configured to control light emission from the light-emitting element.

10. An electronic device comprising:
a display portion comprising:
a light-emitting element comprising the organic compound according to claim 1; and
a control circuit configured to control light emission from the light-emitting element.

11. A fluorene derivative represented by General Formula (G2-1):

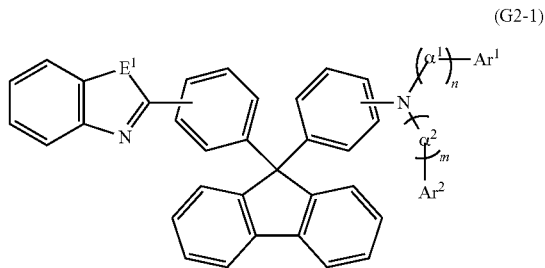

(G2-1)

wherein $E^1$ represents an oxygen atom or a nitrogen atom to which a phenyl group or a biphenyl group is bonded,
wherein m and n separately represent 0 or 1,
wherein $\alpha^1$ and $\alpha^2$ separately represent an arylene group, and
wherein $Ar^1$ and $Ar^2$ separately represent any of a phenyl group, a naphthyl group, a phenanthryl group, and a triphenylenyl group.

12. The fluorene derivative according to claim 11,
wherein the $\alpha^1$ and the $\alpha^2$ separately represent a phenylene group or a biphenyldiyl group.

13. The fluorene derivative according to claim 11,
wherein the $E^1$ represents the nitrogen atom to which a phenyl group is bonded,
wherein n represents 1,
wherein $\alpha^1$ and $\alpha^2$ separately represent a phenylene group, and
wherein $Ar^1$ and $Ar^2$ separately represent a phenyl group.

14. The fluorene derivative according to claim 11, wherein the fluorene derivative is represented by Structural Formula (1) below:

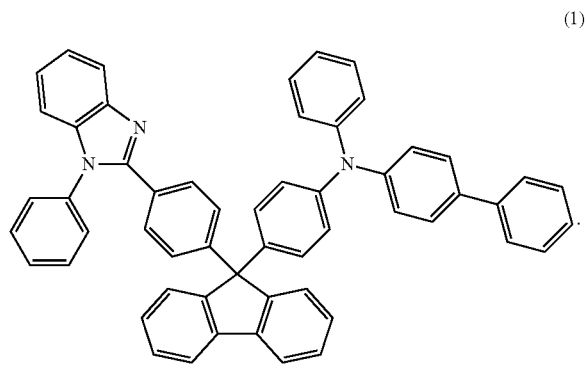 [SMILES: c1ccc(-c2ccc(N(c3ccccc3)c3ccc(C4(c5ccc(-c6nc7ccccc7n6-c6ccccc6)cc5)c5ccccc5-c5ccccc54)cc3)cc2)cc1]

(1)

15. A light-emitting element comprising the fluorene derivative according to claim 11 between a pair of electrodes.

16. A light-emitting element comprising:
a light-emitting layer comprising the fluorene derivative according to claim 11 and a phosphorescent compound, between a pair of electrodes.

17. A light-emitting element comprising:
a layer comprising the fluorene derivative according to claim 11, between a pair of electrodes; and a light-emitting layer comprising a phosphorescent compound, between the layer and one of the pair of electrodes.

18. A light-emitting element comprising a light-emitting layer comprising the fluorene derivative according to claim 11.

19. A light-emitting device comprising:
a light-emitting element comprising the fluorene derivative according to claim 11; and
a control circuit configured to control light emission from the light-emitting element.

20. An electronic device comprising:
a display portion comprising:
a light-emitting element comprising the fluorene derivative according to claim 11; and
a control circuit configured to control light emission from the light-emitting element.

21. A fluorene derivative represented by General Formula (G2-2):

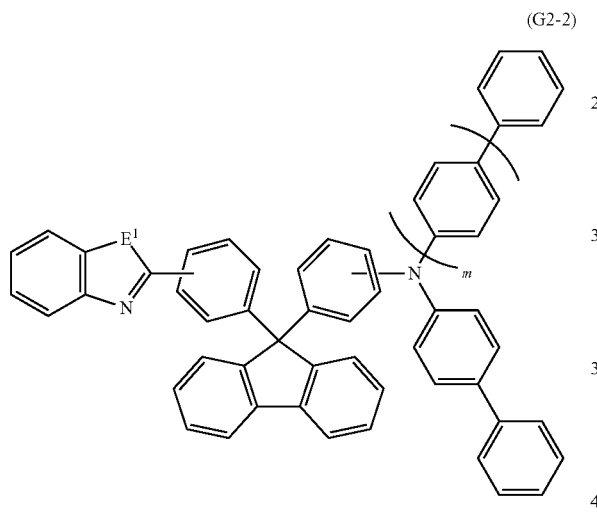

(G2-2)

wherein $E^1$ represents an oxygen atom or a nitrogen atom to which a phenyl group or a biphenyl group is bonded, and wherein m represents 0 or 1.

22. A light-emitting element comprising the fluorene derivative according to claim 21 between a pair of electrodes.

23. A light-emitting element comprising:
a light-emitting layer comprising the fluorene derivative according to claim 21 and a phosphorescent compound, between a pair of electrodes.

24. A light-emitting element comprising:
a layer comprising the fluorene derivative according to claim 21, between a pair of electrodes; and
a light-emitting layer comprising a phosphorescent compound, between the layer and one of the pair of electrodes.

25. A light-emitting element comprising a light-emitting layer comprising the fluorene derivative according to claim 21.

26. A light-emitting device comprising:
a light-emitting element comprising fluorene derivative according to claim 21; and
a control circuit configured to control light emission from the light-emitting element.

27. An electronic device comprising:
a display portion comprising:
a light-emitting element comprising the fluorene derivative according to claim 21; and
a control circuit configured to control light emission from the light-emitting element.

28. The organic compound according to claim 2, wherein the $E_A$ is a phenyl group substituted with a benzimidazole group.

29. The organic compound according to claim 3, wherein the $H_A$ is a diphenylaminophenyl group.

* * * * *

UNITED STATES PATENT AND TRADEMARK OFFICE
CERTIFICATE OF CORRECTION

PATENT NO. : 8,771,843 B2  
APPLICATION NO. : 13/218597  
DATED : July 8, 2014  
INVENTOR(S) : Satoshi Seo et al.

It is certified that error appears in the above-identified patent and that said Letters Patent is hereby corrected as shown below:

In the Specification:

Column 2, Line 7; Change "(HOMO" to --(LUMO--.

Column 5, Line 18; Change "illustrate, a" to --illustrate a--.

Column 9, Line 51; Change "5-phenyllimidazo[" to --5-phenylimidazo[--.

Column 16, Line 43; Change "Formmula" to --Formula--.

Column 20, Line 5; Change "gkeleton" to --skeleton--.

Column 24, Line 8; Change "perforin" to --perform--.

Column 25, Line 13; Change "AlLi);" to --AlLi);--.

Column 25, Line 51; Change ")triphenylamine 0" to --)triphenylamine--.

Column 26, Line 30; Change "NPS" to --NPB--.

Column 26, Line 31; Change "N,N$^1$-bis" to --N,N'-bis--.

Column 27, Lines 6 to 7; Change "]-N-phenylamino}" to --N'-phenylamino}--.

Column 28, Line 2; Change "Flrpic)," to --FIrpic),--.

Column 28, Line 48; Change "N,N-bis" to --N,N'-bis--.

Column 29, Line 66; Change "beryilium" to --beryllium--.

Column 32, Line 11; Change "aimed" to --formed--.

Column 35, Line 64; Change "foamed" to --formed--.

Column 36, Line 29; Change "be, given." to --be given.--.

Column 40, Line 43; Change "bacldight" to --backlight--.

Column 46, Line 15; Change "it conjugation." to --$\pi$ conjugation.--.

Signed and Sealed this  
Eighteenth Day of August, 2015

Michelle K. Lee  
*Director of the United States Patent and Trademark Office*